US012781290B2

(12) United States Patent
Wang et al.

(10) Patent No.: US 12,781,290 B2
(45) Date of Patent: Nov. 3, 2026

(54) PRIMERS AND PROBES AND REAGENT KIT FOR SYNCHRONOUS DETECTION OF CYMMV, ORSV, AND CYMRSV, AND APPLICATIONS THEREOF

(71) Applicants: FLOWER RESEARCH INSTITUTE OF YUNNAN ACADEMY OF AGRICULTURAL SCIENCES, Kunming (CN); YUNNAN UNIVERSITY, Kunming (CN)

(72) Inventors: Lihua Wang, Kunming (CN); Aiqing Sun, Kunming (CN); Xuewei Wu, Kunming (CN); Suping Qu, Kunming (CN); Yiping Zhang, Kunming (CN); Xiumei Yang, Kunming (CN); Yan Su, Kunming (CN); Feng Xu, Kunming (CN); Lifang Zhang, Kunming (CN)

( * ) Notice: Subject to any disclaimer, the term of this patent is extended or adjusted under 35 U.S.C. 154(b) by 404 days.

(21) Appl. No.: 18/401,631

(22) Filed: Jan. 1, 2024

(65) Prior Publication Data

US 2024/0132979 A1 Apr. 25, 2024

(30) Foreign Application Priority Data

Jan. 4, 2023 (CN) ........................ 202310010087.X

(51) Int. Cl.
*C12Q 1/70* (2006.01)
*C12Q 1/6851* (2018.01)

(52) U.S. Cl.
CPC ........... *C12Q 1/701* (2013.01); *C12Q 1/6851* (2013.01); *C12Q 2561/101* (2013.01); *C12Q 2600/16* (2013.01); *C12Q 2600/166* (2013.01)

(58) Field of Classification Search
CPC .................. C12Q 1/701; C12Q 1/6851; C12Q 2600/166; C12Q 2600/16
See application file for complete search history.

(56) References Cited

U.S. PATENT DOCUMENTS

2003/0050470 A1* 3/2003 An ......................... C07H 21/00 435/6.14
2017/0039316 A1* 2/2017 Fofanov ................. G16B 30/10

FOREIGN PATENT DOCUMENTS

CN 113789413 A * 12/2021 ........... C12Q 1/6851
TW I467021 B * 1/2015

OTHER PUBLICATIONS

Grieco F. Cymbidium ringspot virus, complete genome. NCBI Reference Sequence: NC_003532.1. Aug. 13, 2018. (Year: 2018).*
Lee SH, et. al. Odontoglossum ringspot virus gene for coat protein, complete cds. GenBank: AB753720.1. Oct. 10, 2012. (Year: 2012).*
Choi S, Yoon J, Chung B. Cymbidium mosaic virus CP gene for coat protein, complete cds, strain: CK25. GenBank: AB541534.1. Mar. 15, 2012. (Year: 2012).*
Kim SM, Choi SH. Simultaneous detection of Cymbidium mosaic virus and Odontoglossum ringspot virus in orchids using multiplex RT-PCR. Virus Genes. Dec. 2015;51(3):417-22. Epub Nov. 5, 2015. (Year: 2015).*
Takara. Premix Ex Taq™ (Perfect Real Time) Product Manual. Cat. #RR039A. Ver.202202Da. Jun. 11, 2022. (Year: 2022).*

* cited by examiner

*Primary Examiner* — Rachel B Gill

(57) ABSTRACT

A method for detecting CymMV, ORSV, and CymRSV involves designing multiplex real-time quantitative PCR detection primers and probes for CymMV, ORSV, and CymRSV and applying these primers and probes to the real-time quantitative PCR simultaneous detection of CymMV, ORSV, and CymRSV. It allows for faster detection of CymMV, ORSV, and CymRSV, taking only one-third of the time compared to uniplex real-time quantitative PCR technology, thereby reducing testing costs by approximately ⅓ to ½ for each sample. The primers and probes are highly specific and sensitive, with a sensitivity as low as 1 to 10 copies. It provides an efficient and feasible detection method for early detection and prevention of CymMV, ORSV, and CymRSV.

8 Claims, 22 Drawing Sheets

Specification includes a Sequence Listing.

PRIMERS AND PROBES AND REAGENT KIT FOR SYNCHRONOUS DETECTION OF CYMMV, ORSV, AND CYMRSV, AND APPLICATIONS THEREOF

TECHNICAL FIELD

The present disclosure generally relates to a field of pathogen detection technology; more specifically, it pertains to primers and probes and their applications for the simultaneous detection of Cymbidium mosaic virus (CymMV), Odontoglossum ringspot virus (ORSV), and Cymbidium ringspot virus (CymRSV).

BACKGROUND

Orchids such as phalaenopsis orchid have significant ornamental and economic value. In recent years, with the increasing frequency of domestic and international trade and germplasm exchange of orchids such as phalaenopsis orchid, the occurrence and spread of some seed-borne diseases such as viral diseases have been accelerated. Currently, there are more than 30 different viruses that can infect orchids around the world, of which Cymbidium mosaic virus (CymMV) and Odontoglossum ringspot virus (ORSV) are the most common, widespread and damaging to orchids. Most often, orchids can be infected with CymMV or ORSV, or co-infected with CymMV and ORSV, and occasionally, multiple viruses (e.g., three different types of viruses) including CymMV and ORSV can co-infect orchids. Cymbidium ringspot virus (CymRSV) is also one of the more severe types of virus that infect orchids, and currently occurs mainly in Europe, North America, South America, and other places. At present, there is no effective medication available internationally for the prevention and treatment of viral diseases in flowers including the phalaenopsis orchid. To cultivate healthy and high-quality seedlings and ornamental flower products, it is necessary to detect and isolate plants infected with viral diseases at an early stage. Therefore, it is very important to establish an efficient and sensitive method that can simultaneously detect CymMV, ORSV, and CymRSV.

At present, virus detection methods include indicator plant method, enzyme-linked immunosorbent assay (ELISA), electron microscopy technology, reverse transcription loop-mediated isothermal amplification (RT-LAMP), RT-PCR, real-time quantitative PCR (qRT-PCR), among others. The indicator plant method can directly check the leaves and stems of plants for visible virus symptoms. Although the indicator plant method is simple, it takes a long time (the shortest is 10 to 20 days, while the longest is 1 to 3 months), has low sensitivity, is subject to seasonal restrictions, and has high labour and material costs. The electron microscopy method is time-consuming, and requires expensive equipment, and reliable results depend on long-term experience accumulation. The ELISA method has a long periodicity and a sensitivity at the nanogram level making it impossible to detect lower concentrations of the virus. The RT-PCR molecular biology method theoretically has strong specificity and sensitivity at the femtogram level, but there may be false positives due to non-specific amplification of the sample during the PCR process, and it is only used for qualitative detection. The gene chip technology is complex and time-consuming, with high skill requirements for operators, and the production of gene chips is expensive, which greatly limits its promotion. The real-time fluorescence quantitative PCR (qRT-PCR) method utilizes changes in fluorescence signals to detect changes in the amount of amplification product in each cycle of PCR amplification reaction in real-time, and quantitatively analyzes the initial template based on the relationship between Cq value and standard curve. Compared with conventional PCR techniques, qRT-PCR achieves quantitative detection of template content in samples without the need for electrophoresis or other steps. The qRT-PCR has the characteristics of high specificity, good repeatability, shorter processing time, and convenient operation, making it the most sensitive detection method currently available. The multiplex precise real-time fluorescence quantitative PCR method based on the Taqman probe is more cost-effective and time-saving than uniplex qRT-PCR technology while providing high detection sensitivity (1-10 copies). Due to its advantages of speed, efficiency, good specificity, and high sensitivity, the multiplexed precise real-time fluorescence quantitative PCR method has been widely used in the detection of pathogens, parasites, viruses, diseases and transgenic products, as well as in an analysis of gene expression levels, and has a wide development and application space.

CymMV, ORSV, and CymRSV are all single-stranded RNA viruses that are prone to mutation, with many mutation sites between different strains. Therefore, the challenges in detecting CymMV, ORSV, and CymRSV using triplex real-time fluorescence quantitative PCR technology include selecting conservative sequences, designing primer and probe combinations, optimizing the detection system, and implementing strict contamination prevention measures to avoid false positive results during the experiment.

Currently, research on the detection of CymRSV is limited, particularly in the area of multiplex simultaneous detection technology for CymMV, ORSV, and CymRSV in orchids, which has yet to be reported. Developing specific primers and probes for triplex real-time fluorescence quantitative PCR capable of simultaneously detect CymMV, ORSV, and CymRSV is a significant challenge. Furthermore, providing a fast, efficient, stable, and reliable triplex real-time fluorescence quantitative PCR detection method is crucial. Such advancements are essential for cultivating healthy and high-quality orchid seedlings, enabling early detection, isolation and prevention of virus-carrying seedlings or potted flowers. This progress would significantly enhance product quality and corporate economic benefits for enterprises, addressing an urgent technical problem to be solved.

SUMMARY

To overcome the disadvantages in the background, the present disclosure provides primers and probes for real-time quantitative PCR (Polymerase Chain Reaction) for the simultaneous detection of Cymbidium mosaic virus (CymMV), Odontoglossum ringspot virus (ORSV), and Cymbidium ringspot virus (CymRSV), as well as their applications. This innovation achieves rapid, highly sensitive, and specific quantitative detection while significantly reducing costs. It offers technical support for the early detection and prevention of CymMV, ORSV, and CymRSV in orchids.

To achieve the above objectives, the present invention is implemented through the following technical solutions:

This specification provides a set of primers and probes for the simultaneous detection of CymMV, ORSV, and CymRSV. The primers and probes include: a forward primer CymMV-F, a reverse primer CymMV-R and a probe CymMV-P for CymMV; a forward primer ORSV-F, a reverse primer ORSV-R and a probe ORSV-P for ORSV; a forward primer CymRSV-F, a reverse primer CymRSV-R and a probe CymRSV-P for CymRSV;

```
For CymMV:
the forward primer CymMV-F:
                                        (SEQ ID NO: 1)
5'-CTGATGCTGGCCACTAACGA-3';

the reverse primer CymMV-R:
                                        (SEQ ID NO: 2)
5'-CACGTTCACGGTCAGTAGGG-3';

the probe CymMV-P:
                                        (SEQ ID NO: 3)
FAM-CCGCCAACTGGGCCAAGGCT-BHQ1.

For ORSV:
the forward primer ORSV-F:
                                        (SEQ ID NO: 4)
5'-TTGACCAGTAGGTTCCCTGC-3';

the reverse primer ORSV-R:
                                        (SEQ ID NO: 5)
5'-TAGTTGTCGGATTCTGCGGAT-3';

the probe ORSV-P:
                                        (SEQ ID NO: 6)
HEX-TGGTTACTTCAGAGTTTATCGCTATG-BHQ1.

For CymRSV:
the forward primer CymRSV-F:
                                        (SEQ ID NO: 7)
5'-CGCAGTGGGTGACTTATT-3';

the reverse primer CymRSV-R:
                                        (SEQ ID NO: 8)
5'-CGTCGTGGCTGTGGTAG-3';

the probe CymRSV-P0:
                                        (SEQ ID NO: 9)
Cy5-CACAGTAACCTTCTACGAACCGCAACCG-BHQ3.
```

This specification further provides a real-time fluorescence quantitative PCR amplification system, which includes 12.5 μL of Premix Ex Taq (2×) mixture and 3.7 μL of RNase-free $ddH_2O$.

This specification also provides an application assay using the set of primers and probes for the simultaneous detection of CymMV, ORSV, and CymRSV, utilizing the primers and probes as previously described above.

Furthermore, this specification provides a reagent kit for simultaneous detection of CymMV, ORSV, and CymRSV, which includes the primers and probes for simultaneous detection as described above and the real-time fluorescence quantitative PCR amplification assay as described above.

At least one embodiment of the present disclosure has the following beneficial effects:

By utilizing multiplex real-time fluorescence quantitative PCR primers and probes designed for simultaneous detection of CymMV, ORSV, and CymRSV in phalaenopsis orchid, these viruses can be detected more rapidly and accurately. This method requires only one-third the time of uniplex real-time fluorescence quantitative PCR technology, and reduces detection cost by about ⅓ to ½ per sample. With its strong specificity and high sensitivity, capable of detecting as few as 1-10 copies, this approach offers an efficient and practical solution for the early detection and prevention of CymMV, ORSV, and CymRSV. Such advancements are crucial for the industrial production of high-quality and healthy orchid seedlings, including phalaenopsis orchid.

BRIEF DESCRIPTION OF THE DRAWINGS

In order to provide a clearer explanation of the technical solutions in the embodiments or the prior art described in this specification, a brief introduction of the drawings required in the embodiments or the prior art description will be provided below. It is evident that the following description only represents a portion of the embodiments recorded in this application. For ordinary technical personnel in this field, they can also obtain other drawings based on these drawings without any creative work.

In FIG. 7 to FIG. 9, A represents positive sample with three types of viruses, B represents test sample carrying three types of viruses (CymMV, ORSV and CymRSV), C represents test sample carrying CymMV and ORSV, D represents test sample carrying CymMV, E represents test sample carrying ORSV, F represents test sample carrying CymRSV, G-J represents test sample carrying CMV, TMV, CarMV, LMoV, respectively, "K" represents negative sample, L represents $H_2O$.

Figure 16:
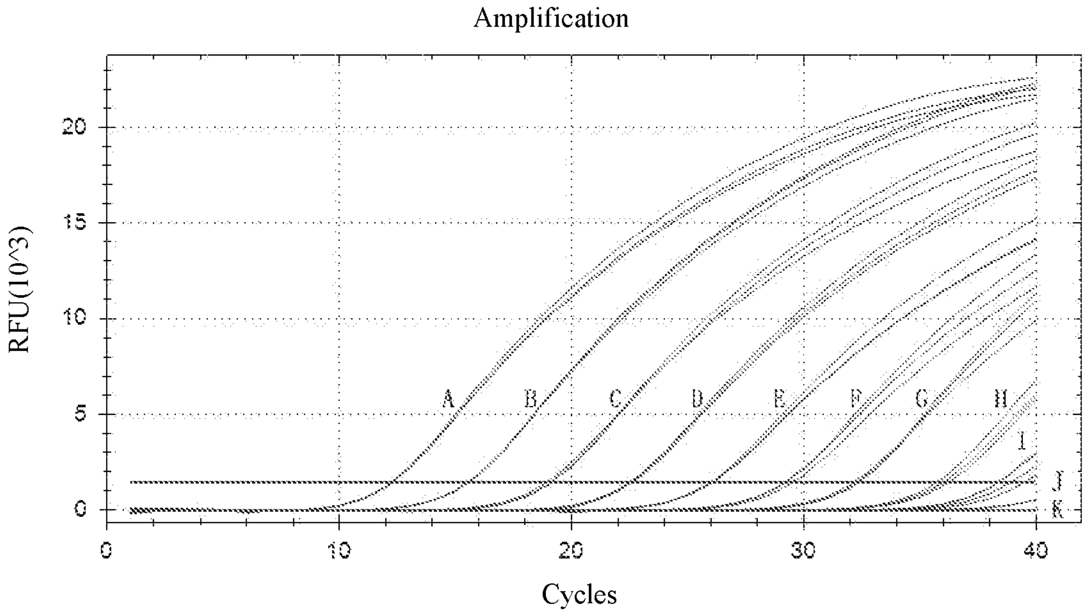
FIG. 16 represents the sensitivity amplification curve for CymMV (FAM channel) of the multi-target simultaneous real-time fluorescence quantitative PCR established in Embodiment 6 of this specification.
Figure 17:
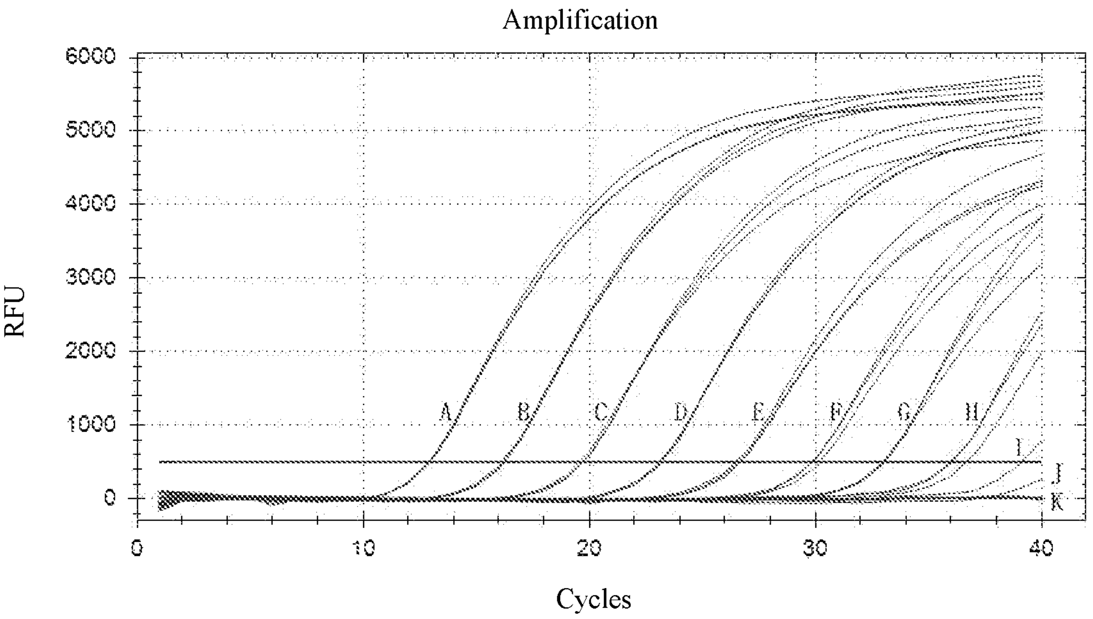
FIG. 17 represents the sensitivity amplification curve for ORSV (HEX channel) of the multiplex real-time fluorescence quantitative PCR established in Embodiment 6 of this specification.
Figure 18:
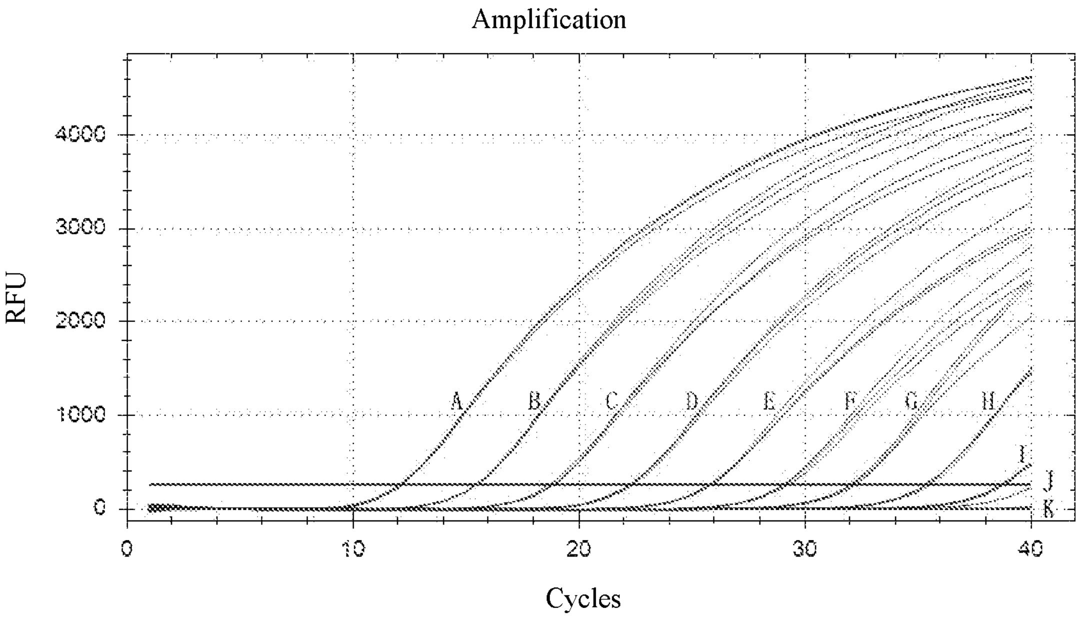
FIG. 18 represents the sensitivity amplification curve for CymRSV (Cy5 channel) of the multiplex real-time fluorescence quantitative PCR established in Embodiment 6 of this specification.

In these figures (FIG. 16 to FIG. 18), A: $1\times10^9$ copies; B: $1\times10^8$ copies; C: $1\times10^7$ copies; D: $1\times10^6$ copies; E: $1\times10^5$ copies; F: $1\times10^4$ copies; G: $1\times10^1$ copies; H: $1\times10^2$ copies; I:1×10 copies; J:1 copy; K: $H_2O$.

Figure 19:
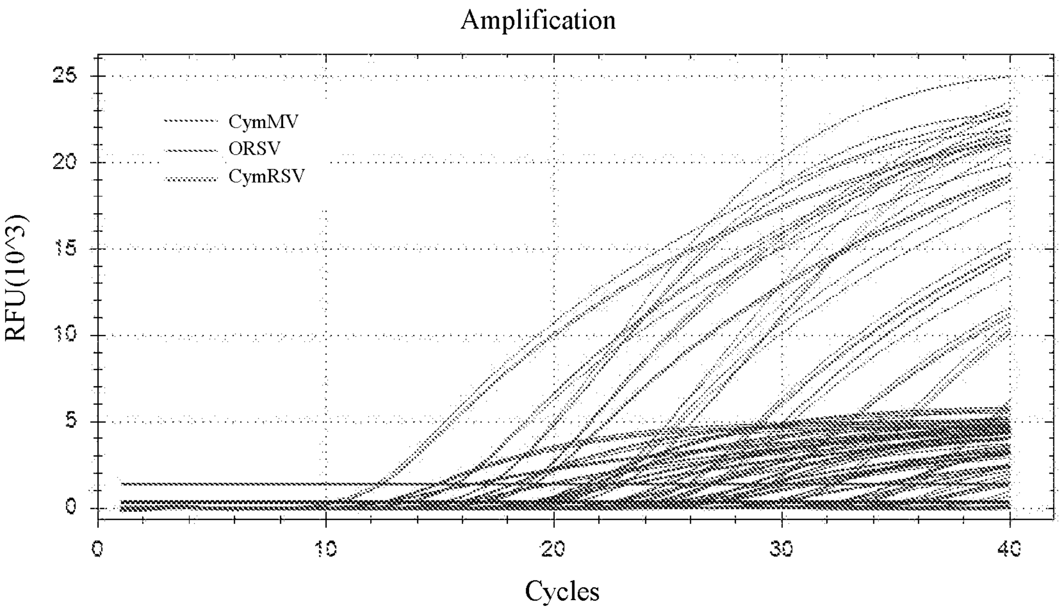

FIG. 19 represents an overall figure presenting amplification curves (FIG. 20-FIG. 22) of the real-time fluorescence quantitative PCR obtained through three parallel experiments on 8 plasmid standards with mixed viruses, positive sample, and negative sample, as provided in Embodiment 7 of this specification.

Figure 20:
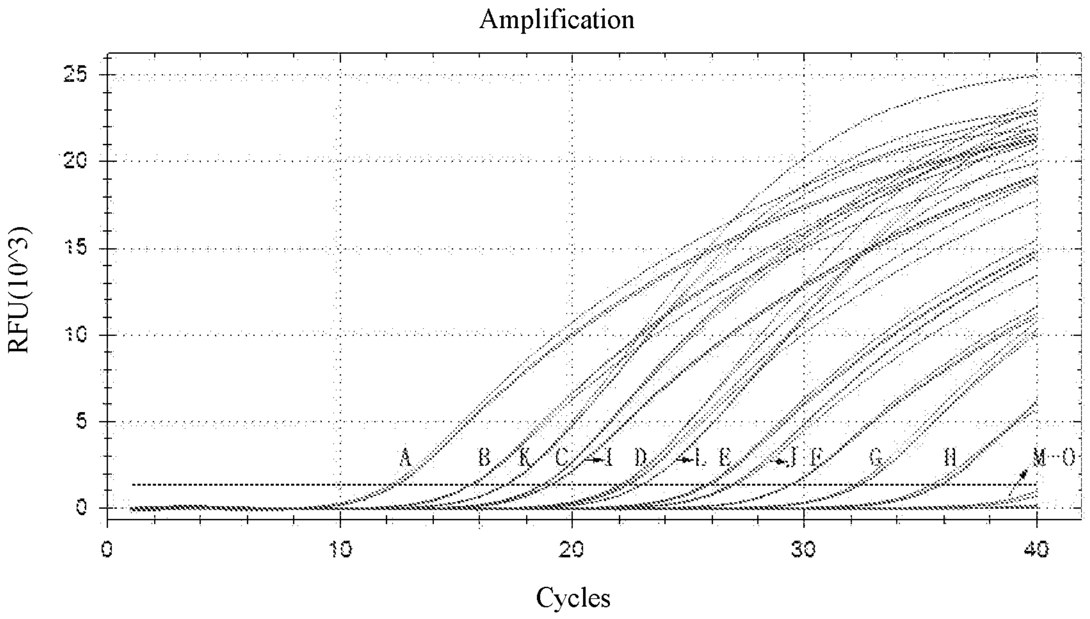

FIG. 20 represents the amplification curve for CymMV (FAM channel) of the real-time fluorescence quantitative PCR obtained through three parallel experiments on 8 plasmid standards with mixed viruses, positive sample, and negative sample, as provided in Embodiment 7 of this specification.

Figure 21:
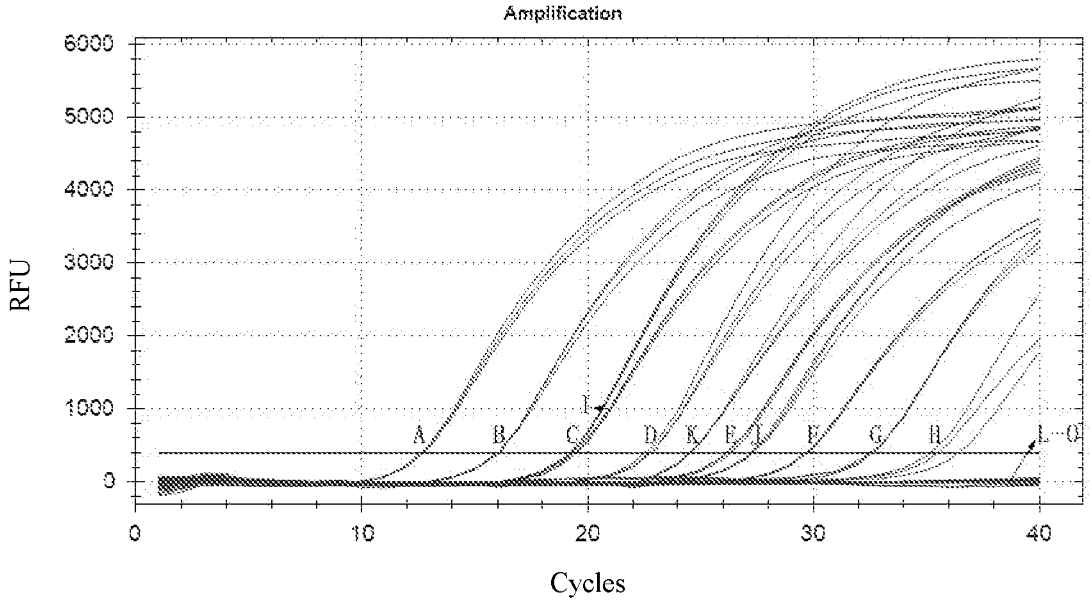

FIG. 21 represents the amplification curve for ORSV (HEX channel) of the real-time fluorescence quantitative PCR obtained through three parallel experiments on 8 plasmid standards with mixed viruses, positive sample, and negative sample, as presented in Embodiment 7.

Figure 22:
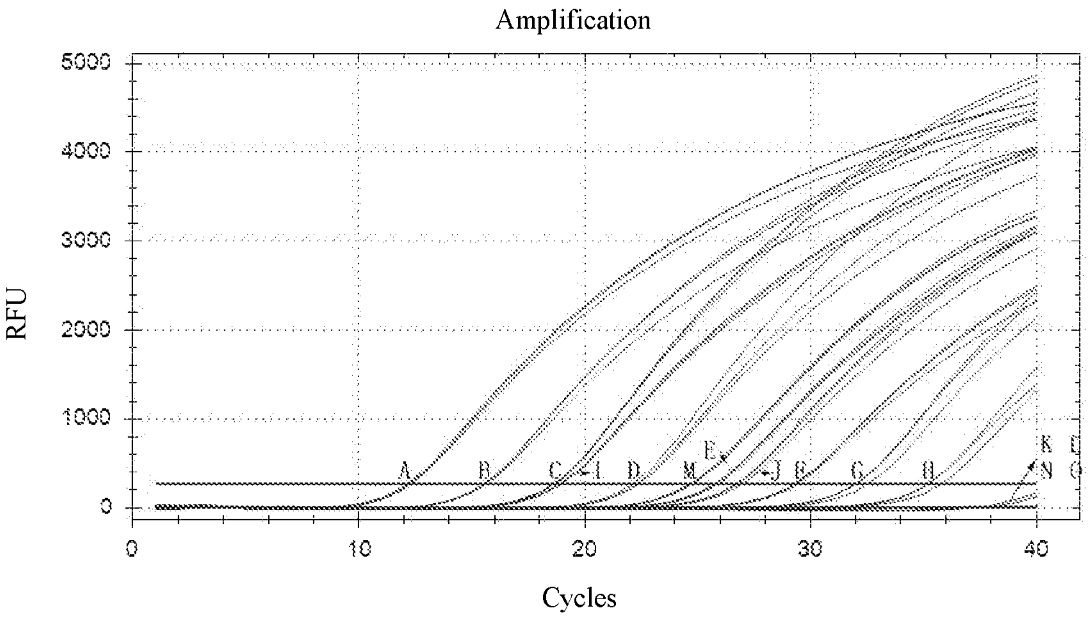

FIG. 22 represents the amplification curve for CymRSV (Cy5 channel) of the real-time fluorescence quantitative PCR obtained through three parallel experiments on 8 plasmid standards with mixed viruses, positive sample, and negative sample, as outlined in Embodiment 7.

In these figures (FIG. 20 to FIG. 22), A represents $1\times10^9$ copies; B represents $1\times10^8$ copies; C represents $1\times10^7$ copies; D represents $1\times10^6$ copies; E represents $1\times10^5$ copies; F represents $1\times10^4$ copies; G represents $1\times10^3$ copies; H represents $1\times10^2$ copies; I represents positive sample containing all three viruses; J represents test sample carrying all three viruses; K represents test sample carrying CymMV and ORSV; L represents test sample carrying CymMV; M represents test sample carrying CymRSV; N represents negative sample; O represents $H_2O$.

DETAILED DESCRIPTION OF EMBODIMENTS

To provide a clear and comprehensive description of the technical solutions in one or more embodiments of this specification, the embodiments will be described in detail in conjunction with the specific embodiments and the corresponding drawings in this specification. Clearly, the described embodiments are only a part of the embodiments in this specification, not all of them. Based on the embodiments in this specification, all other embodiments obtained by those skilled in the art without creative effort are within the scope of protection of one or more embodiments of this specification.

The technical solutions provided by various embodiments of this specification will be described in detail below with reference to the drawings.

The present invention designs primers and probes for specific detection based on the the conserved sequences of the coat protein genes (CP) of CymMV, ORSV, and CymRSV A triplex real-time fluorescence quantitative PCR detection technology system for CymMV, ORSV, and CymRSV has been established by optimizing reaction conditions. The invention provides fluorescence quantitative PCR primers and probes for simultaneous detection of CymMV, ORSV, and CymRSV in phalaenopsis orchid, including:

```
For CymMV:
forward primer CymMV-F:
                                  (SEQ ID NO: 1)
5'-CTGATGCTGGCCACTAACGA-3'.

reverse primer CymMV-R:
                                  (SEQ ID NO: 2)
5'-CACGTTCACGGTCAGTAGGG-3'.

probe CymMV-P:
                                  (SEQ ID NO: 3)
FAM-CCGCCAACTGGGCCAAGGCT-BHQ1.
```

The fluorescence group of CymMV-P is FAM, and the quenching group is BHQ1.

```
For ORSV:
forward primer ORSV-F:
                                  (SEQ ID NO: 4)
5'-TTGACCAGTAGGTTCCCTGC-3'.

reverse primer ORSV-R:
                                  (SEQ ID NO: 5)
5'-TAGTTGTCGGATTCTGCGGAT-3'.

Probe ORSV-P:
                                  (SEQ ID NO: 6)
HEX-TGGTTACTTCAGAGTTTATCGCTATG-BHQ1.
```

The fluorescence group of ORSV-P is HEX, and the quenching group is BHQ1.

```
For CymRSV:
forward primer CymRSV-F:
                                  (SEQ ID NO: 7)
5'-CGCAGTGGGTGACTTATT-3'.

reverse primer CymRSV-R:
                                  (SEQ ID NO: 8)
5'-CGTCGTGGCTGTGGTAG-3'.

probe CymRSV-P:
                                  (SEQ ID NO: 9)
Cy5-CACAGTAACCTTCTACGAACCGCAACCG-BHQ3.
```

The fluorescence group of CymRSV-P is Cy5, and the quenching group is BHQ3.

The invention also provides a real-time fluorescence quantitative PCR amplification system, which may include 12.5 μL of Premix Ex Taq (2×) mixture and 3.7 μL of RNase-free $ddH_2O$.

The invention further provides an application of the primers and probes for simultaneous detection of CymMV, ORSV, and CymRSV in orchids, using the real-time fluorescence quantitative PCR amplification system described above. The detection method for rapid detection of CymMV, ORSV, and CymRSV in orchids can include the following steps:

(1) Obtaining leaf, flower stalk, or other tissue from a test sample to extract total RNA.

(2) Using the extracted total RNA as a template for reverse transcription to obtain cDNA.

(3) Using the cDNA obtained in step (2) as a test template, the primers and probes for simultaneous detection of CymMV, ORSV, and CymRSV are used to perform real-time fluorescence quantitative PCR amplification in the amplification system described above, to obtain the amplification curves for CymMV, ORSV, and CymRSV.

(4) Calculating the copy numbers of CymMV, ORSV, and CymRSV carried by the test sample based on the Cq values of CymMV, ORSV, and CymRSV, respectively, using the standard curve equations provided in the description.

The standard curve equations for CymMV, ORSV, and CymRSV are as follows:

CymMV: $y=-3.336x+41.789(E=99.4\%, R^2=0.999)$.

ORSV: $y=-3.319x+41.901(E=100.1\%, R^2=0.999)$.

CymRSV: $y=-3.332x+41.202(E=99.6\%, R^2=0.999)$.

In these equations, "E" represents the amplification efficiency, and "$R^2$" represents the coefficient of determination.

Alternatively, based on the amplification curves and Cq values of CymMV, ORSV, and CymRSV, the method for determining the presence of CymMV, ORSV, and CymRSV in the test sample can include the following criteria:

if there is no amplification curve for CymMV, ORSV, and CymRSV of the test sample after the real-time fluorescence quantitative PCR amplification cycle reactions, then CymMV, ORSV, and CymRSV are determined to be negative;

if any of the Cq values of CymMV, ORSV, or CymRSV is less than or equal to 35, then the virus corresponding to the Cq value less than or equal to 35 is determined to be positive;

if any of the Cq values of CymMV, ORSV, or CymRSV is within a range of (35,40], a retest is performed to obtain a first test result, and if the first test result indicates that the Cq value previously within the range of (35,40] is still within the range of (35,40] or less than 35, then the virus corresponding to the Cq value within the range of (35,40] or less than 35 is determined to be positive.

Optionally, performing real-time quantitative PCR amplification cycle reactions within a real-time quantitative PCR amplification system may include:

Constructing an amplification reaction system. The amplification reaction system can be a 25 μL real-time quantitative PCR amplification reaction system, wherein, the optimal primer amounts for CymMV, ORSV, and CymRSV are 20 μM 0.5 μL, 10 μM 0.6 μL, and 20 M 0.6 μL, respectively, and the optimal probe amounts are 10 μM 1.0 μL, 10 μM 1.2 μL, and 10 μM 1.2 μL for CymMV, ORSV, and CymRSV, respectively.

Using the amplification reaction system to perform an amplification cycle reaction.

As an optimal choice, a 25 μL real-time fluorescence quantitative PCR reaction system can specifically include: Premix Ex Taq (2×) mixture 12.5 μL, RNase-free dd$H_2O$ 3.7 μL, 20 M of CymMV-F 0.5 μL, 20 μM of CymMV-R 0.5 μL, 10 μM of CymMV-P 1.0 μL, 10 μM of the ORSV-F 0.6 μL, 10 μM of ORSV-R 0.6 μL, 10 μM of ORSV-P 1.2 μL, 20 μM of CymRSV-F 0.6 μL, 20 μM of CymRSV-R 0.6 μL, 10 μM of CymRSV-P 1.2 μL, the template cDNA 2 μL.

Optionally, the real-time fluorescence quantitative PCR amplification cycling process can include:

pre-denaturation within a temperature range of 94° C. to 95° C. for 30 seconds;

denaturation within a temperature range of 94° C. to 95° C. for 5 seconds, annealing within a temperature range of 58° C. to 60° C. for 30 seconds, performing 40 amplification cycles.

As a preference, pre-denaturation at 95° C. for 30 seconds; denaturation at 95° C. for 5 seconds, annealing at 59° C. for 30 seconds, performing 40 amplification cycles.

The invention also provides a reagent kit for simultaneous detection of CymMV, ORSV, and CymRSV in orchids. The kit includes the primers and probes for simultaneous detection of CymMV, ORSV, and CymRSV as described and the real-time fluorescence quantitative PCR amplification system as described.

To enhance the understanding of the invention, the following embodiments provide a detailed description of the technical solutions of the invention. It should be noted that the described embodiments represent only a portion of the possible embodiments of the invention. All other embodiments derived by those skilled in the art without any creative effort, are considered to be within the scope of this invention.

The main reagents and equipment used for the experiments in the following embodiments may include:

1. Reagents: RNA extraction kit: Mini BEST Plant RNA Extraction Kit (Catalog Number: 9769), reverse transcription kit: PrimeScript RT reagent Kit with gDNA Eraser (Catalog Number: RR047A), PCR kit: Ex Taq (Catalog Number: RR001A), gel recovery kit: Mini BEST Agarose Gel DNA Extraction Kit Ver. 4.0 (Catalog Number: 9760), cloning vector: pMD19-T Vector Cloning Kit (Catalog Number: 6013), *Escherichia coli* competent cells: *E. coli* DH5a Competent Cells (Catalog Number: 9057), and plasmid extraction kit: Mini BEST Plasmid Purification Kit Ver. 4.0 (Catalog Number: 9760), and real-time fluorescence quantitative PCR reagent kit (Catalog Number: RR390A).

2. Equipment: ultramicro ultraviolet spectrophotometer (Thermo ND2000), PCR instrument (Bio-Rad), real-time fluorescence quantitative PCR instrument CFX96 (Bio-Rad).

Embodiment 1

Design of Primers and Probes (1) Extraction and reverse transcription of total RNA from phalaenopsis orchid:

Take 50-100 mg of leaves form phalaenopsis orchid, use a plant RNA extraction kit to extract total RNA from samples, and then use a reverse transcription kit to obtain cDNA.

(2) Design and synthesis of primers and probes:

Downloaded the coat protein sequences of CymMV, ORSV, and CymRSV from NCBI, compare the sequences of using DNAMAN software to find the highly conserved regions of each virus, using Primer 5.0 software to design 3 pairs of specific primers and probes for each virus in highly conserved regions according to qRT-PCR primer design requirements, and Primer-BLAST alignment is performed in NCBI to ensure primer specificity.

Verify the specific primers for qRT-PCR by RT-PCR. Select primers that can produce bright and single bands, good melting curves and high amplification efficiency, and synthesize their corresponding probes. The sequence is shown in Table 1.

TABLE 1

Primers and Probes Sequences

| Primer Name | Sequence (5'-3') | fragment length (bp) |
|---|---|---|
| CymMV-F | CTGATGCTGGCCACTAACGA (SEQ ID NO: 1) | 156 |
| CymMV-R | CACGTTCACGGTCAGTAGGG (SEQ ID NO: 2) | |
| CymMV-P | FAM-CCGCCAACTGGGCCAA GGCT-BHQ1 (SEQ ID NO: 3) | |
| ORSV-F | TTGACCAGTAGGTTCCCTGC (SEQ ID NO: 4) | 148 |
| ORSV-R | TAGTTGTCGGATTCTGCGGAT (SEQ ID NO: 5) | |
| ORSV-P | HEX-TGGTTACTTCAGAGTT TATCGCTATG-BHQ1 (SEQ ID NO: 6) | |
| CymRSV-F | CGCAGTGGGTGACTTATT (SEQ ID NO: 7) | 145 |
| CymRSV-R | CGTCGTGGCTGTGGTAG (SEQ ID NO: 8) | |
| CymRSV-P | Cy5-CACAGTAACCTTC TACGAACCGCAACCG-BHQ3 (SEQ ID NO: 9) | |

Embodiment 2

Preparation of Plasmid Standards of the Three Viruses (1) Using cDNA as Template, Perform PCR Amplification Using the Designed Primers.

The total volume of the amplification reaction system can be 25.0 μL, specifically including: 10×Ex Taq Buffer 2.5 μL, dNTP Mixture 2.5 μL, Ex Taq 0.25 μL, forward primer 0.5 μL, reverse primer 0.5 μL, cDNA 2.5 μL, RNase Free $ddH_2O$ 16.25 μL. Mix the above mixture slowly and carry out the amplification reaction under the following conditions: 95° C. for 5 min; 94° C. for 30 s, annealing at Tm for 30 s (Tm(CymMV)=58° C., Tm(ORSV)=58° C., Tm(CymRSV)=55° C.); 72° C. for 1 min, for 35 cycles; 72° C. for 10 min, and hold at 4° C. Use 1% agarose gel to purify the PCR product.

(2) Ligation and Transformation of Purified PCR Product:

Reaction system 10.0 μL: pEASY-T1 Simple Cloning Vector 1 μL, gel-purified product 4 μL, Solution I 5 μL. Mix the above mixture evenly, and leave at room temperature for 1 hour for a ligation reaction. Quickly transform the ligated plasmid into DH5α competent cells and spread them evenly on LB plates. After 12-16 hours, pick single colonies. Place a single colony in 3 mL LB liquid medium and culture on a shaker at 37° C. (200 rpm) for 12-16 hours, then perform sequencing. Select positive clone samples with completely correct sequences in the sequencing results, and use a plasmid extraction kit to complete the plasmid extraction. Use Hind III to perform enzyme cutting on the extracted plasmid and take 5 μL of the product for agarose gel and gel-purified.

(3) Conversion of Plasmid Concentration to Copy Number:

Measure the plasmid concentration of the gel-extracted plasmid using a spectrophotometer. The concentrations of CymMV, ORSV, and CymRSV are 79.1 ng/μL, 24 ng/μL, and 33.1 ng/μL, respectively. The base count of the pMD-19T vector is 2692 bp, and the average molecular weight is 660 Daltons/bp per base. The sizes of the CymMV, ORSV, and CymRSV amplification products are 156 bp, 148 bp, and 145 bp, respectively. Calculate the gene copy number (copies) in each L sample according to the formula: sample copies/μL=Avogadro's constant $(6.02\times10^{23})\times$plasmid concentration (ng/μL)$\times10^{-9}$/(660×total base count of recombinant plasmid), wherein the total base count of recombinant plasmid=vector sequence base count+insert sequence base count. The calculated copy numbers for CymMV, ORSV, and CymRSV are: $2.5\times10^{10}$ copies/μL, $7.7\times10^{9}$ copies/μL, and $1.06\times10^{10}$ copies/μL, respectively. Dilute the copy numbers to be $5\times10^{9}$ copies/μL. Mix the diluted plasmids of CymMV, ORSV, and CymRSV at equal concentrations and proportions to obtain a plasmid containing $5\times10^{9}$ copies/μL of the three viruses.

Embodiment 3

Establishment and Optimization of Real-Time Fluorescence Quantitative PCR Amplification Reaction System (1) Amplification Reaction System:

Premix Ex Taq (2×) mixture 12.5 μL, 20 μM of CymMV-F 0.5 μL-0.6 μL, 20 μM of CymMV-R 0.5 μL-0.6 μL, 10 μM of CymMV-P 1.0 μL-1.2 μL, 10 μM of ORSV-F 0.5 μL-0.7 μL, 10 μM of ORSV-R 0.5 μL-0.7 μL, 10 μM of ORSV-P 1.0 μL-1.4 μL, 20 μM of CymRSV-F 0.5 μL-0.6 μL, 20 μM of CymRSV-R 0.5 μL-0.6 μL, 10 μM of CymRSV-P 1.0 μL-1.2 μL, RNase free $ddH_2O$ add to 25 μL. The template is the plasmid standards of the three virus obtained in Embodiment 2. Dilute the plasmid gradient to 8 concentrations: $5\times10^{8}$, $5\times10^{7}$, $5\times10^{6}$, $5\times10^{5}$, $5\times10^{4}$, $5\times10^{3}$, $5\times10^{2}$, $5\times10^{1}$ copies/μL. The template additional amount for each concentration is 2 μL. The amplification program, that is, the amplification cycle reaction process includes: pre-denaturation at 94° C.-95° C. for 30 s; denaturation at 94° C.-95° C. for 5 s, annealing at 59° C.-60° C. for 30 s, the number of amplification cycle reactions can be 40. Fluorescence signals of FAM, HEX, and Cy5 are collected at the end of each cycle.

Figure 1:
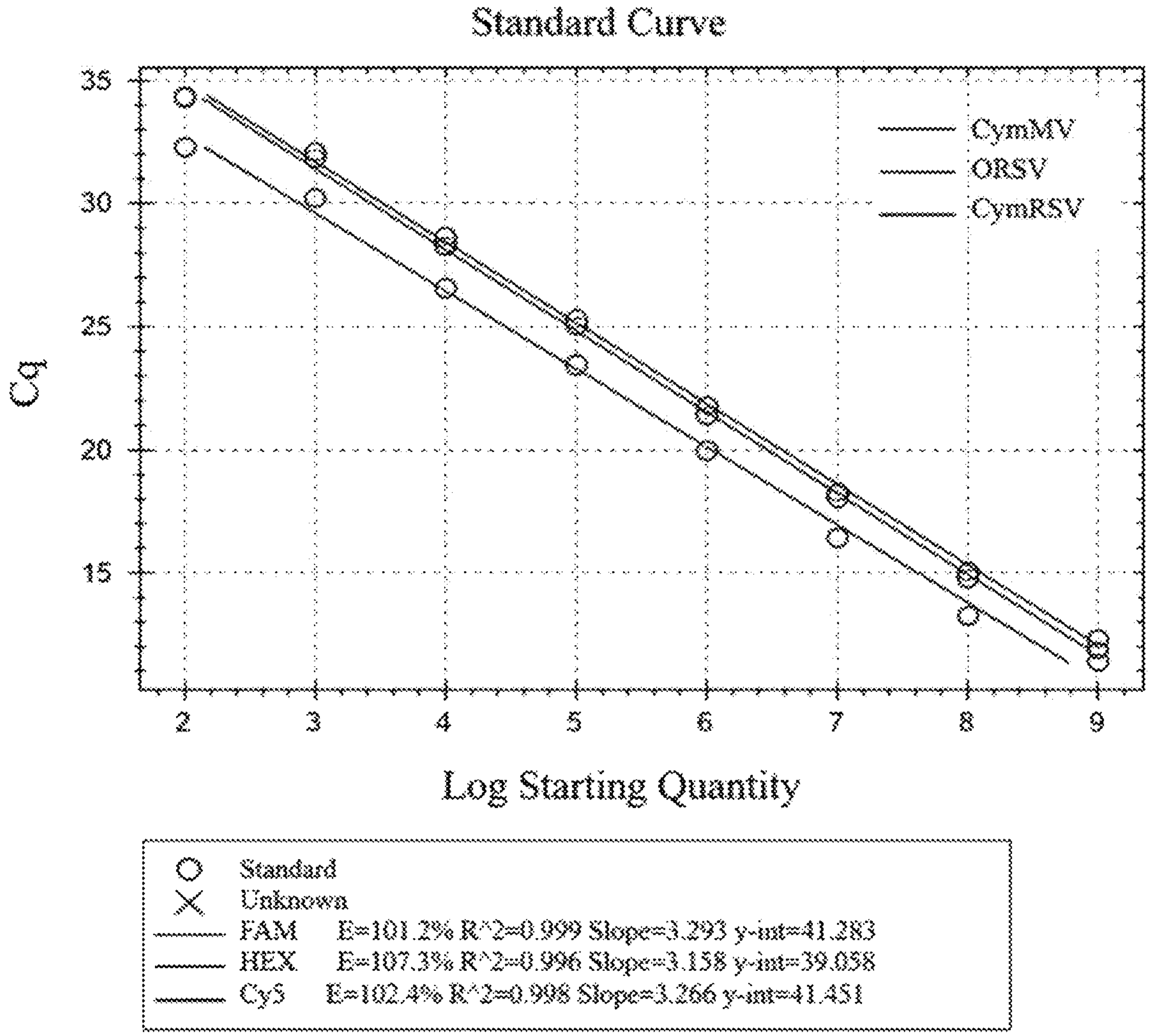
FIG. 1 represents the optimized amplification curves of the real-time fluorescence quantitative PCR system for CymMV, ORSV, and CymRSV provided by a first parameter optimization method in Embodiment 3 of this specification.

(2) System Optimization:

Using cDNA as template, specific primers and probes are used to screen the real-time fluorescence quantitative PCR amplification system and program, and optimization is carried out by fine-tuning the amount of primers, probes and annealing temperature; specifically:

The first parameter optimization method: the amount of primers for CymMV, ORSV, and CymRSV in the amplification reaction system are all 0.5 μL, the amount of probes for CymMV, ORSV, and CymRSV are all 1.0 μL, and the Tm is 59° C. The obtained optimized amplification standard curves of real-time fluorescence quantitative PCR systems for CymMV, ORSV, and CymRSV with different plasmid concentrations are shown in FIG. 1.

Figure 2:
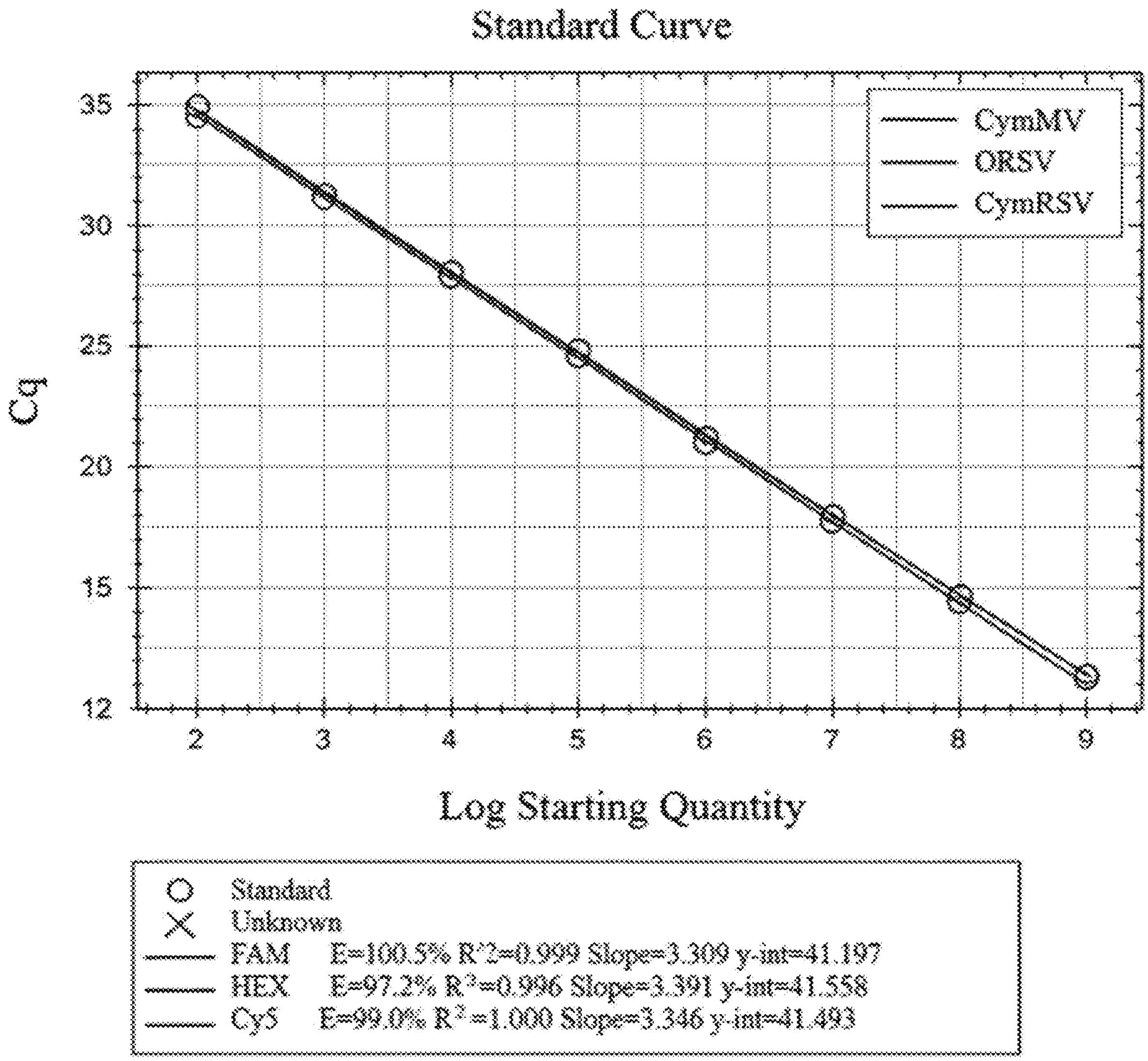
FIG. 2 represents the optimized amplification curves of the real-time fluorescence quantitative PCR system for CymMV, ORSV, and CymRSV provided by a second parameter optimization method in Embodiment 3.

The second parameter optimization method: the amount of primers for CymMV, ORSV, and CymRSV in the amplification reaction system are all 0.5 μL, the amount of probes for CymMV, ORSV, and CymRSV are all 1.0 μL, and the Tm is 60° C. The obtained optimized amplification standard curves of real-time fluorescence quantitative PCR systems for CymMV, ORSV, and CymRSV with different plasmid concentrations are shown in FIG. 2.

Figure 3:
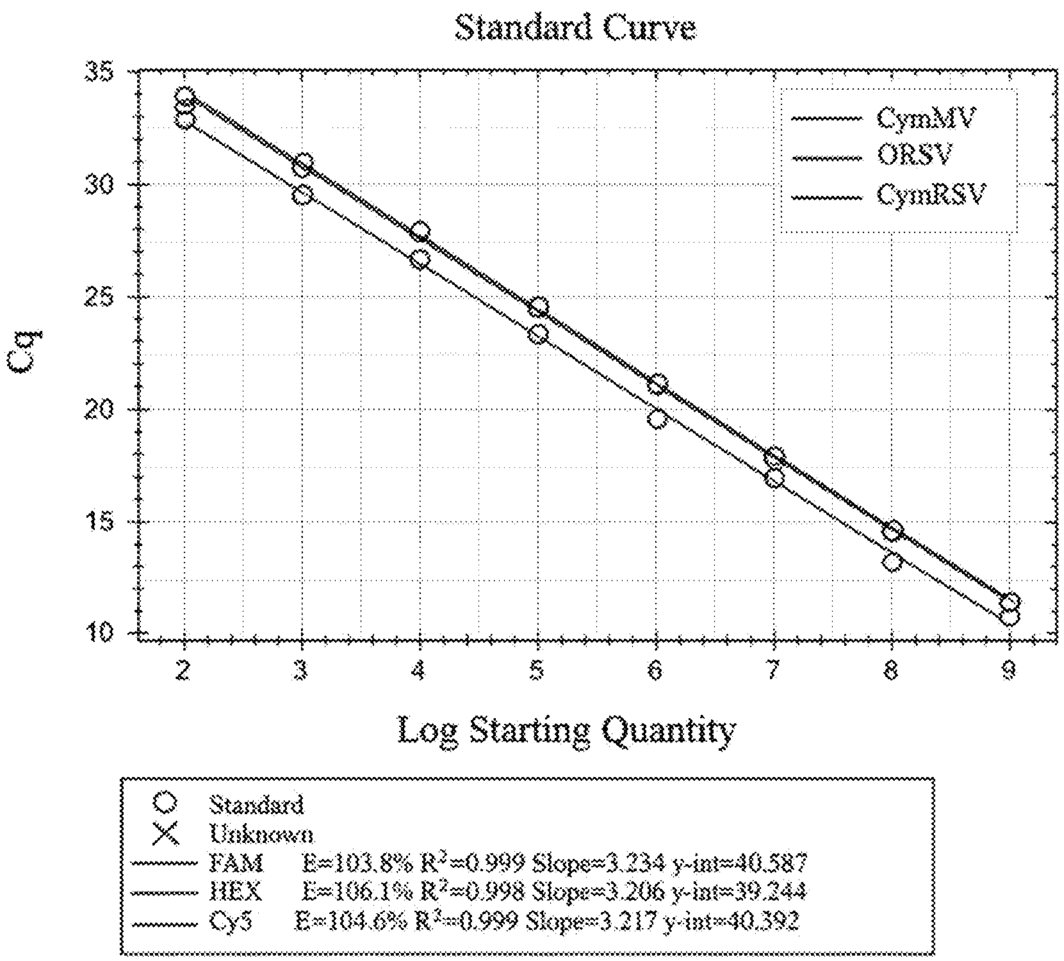
FIG. 3 represents the optimized amplification curves of the real-time fluorescence quantitative PCR system for CymMV, ORSV, and CymRSV provided by a third parameter optimization method in Embodiment 3.

The third parameter optimization method: the amount of primer for CymMV in the amplification reaction system is 0.5 μL, the amount of probe for CymMV is 1.0 μL, the amount of primers for ORSV and CymRSV are both 0.6 μL, the amount of probes for ORSV and CymRSV is 1.2 μL, and the Tm is 59° C. The obtained optimized amplification standard curves of real-time fluorescence quantitative PCR systems for CymMV, ORSV, and CymRSV with different plasmid concentrations are shown in FIG. 3.

Figure 4:
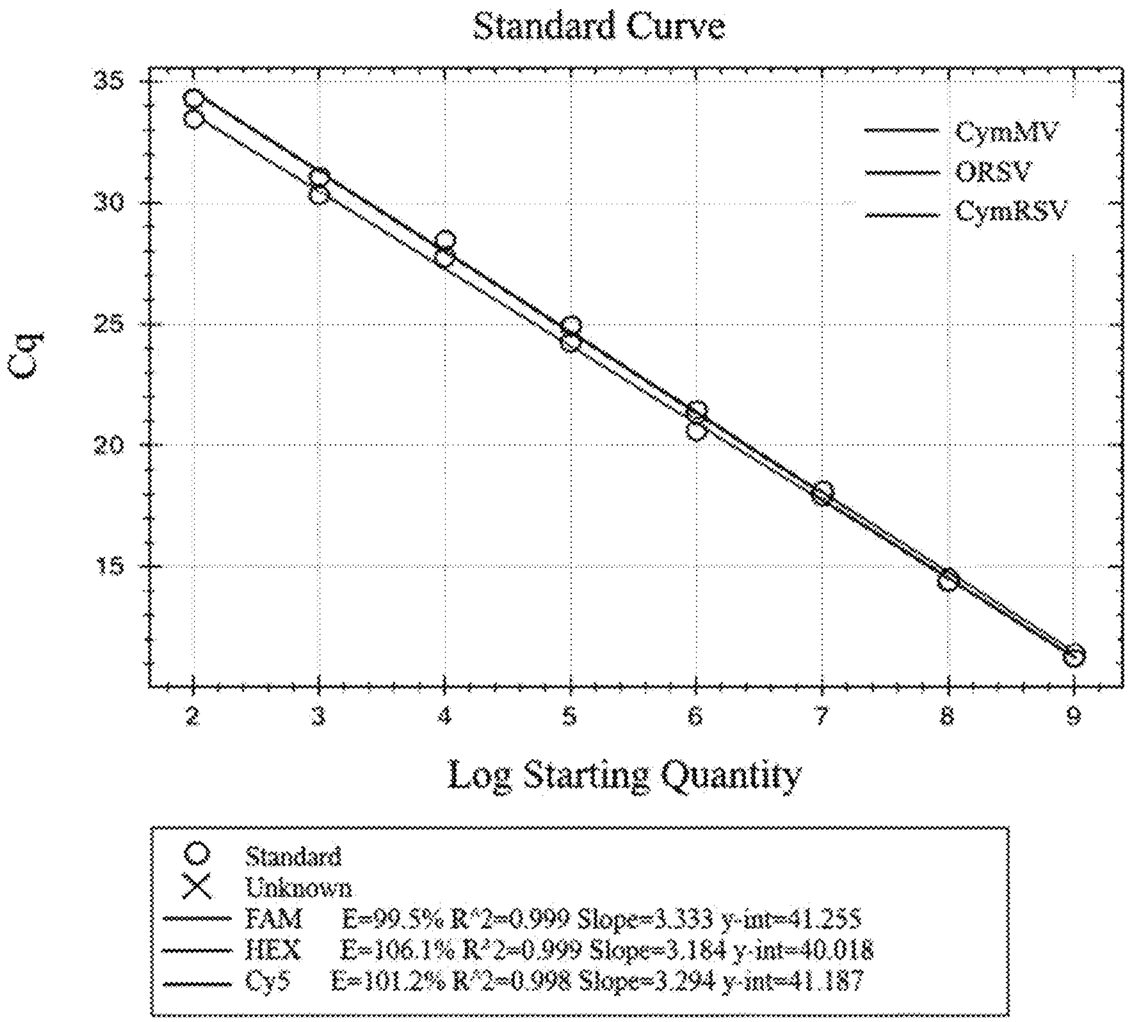
FIG. 4 represents the optimized amplification curves of the real-time fluorescence quantitative PCR system for CymMV, ORSV, and CymRSV provided by a fourth parameter optimization method in Embodiment 3.

The fourth parameter optimization method: the amount of primer for CymMV in the amplification reaction system is 0.5 μL, the amount of probe for CymMV is 1.0 μL, the amount of primer for ORSV and CymRSV are both 0.6 μL, the amount of probe for ORSV and CymRSV is 1.2 μL, and the Tm is 60° C. The obtained optimized amplification standard curves of real-time fluorescence quantitative PCR systems for CymMV, ORSV, and CymRSV with different plasmid concentrations are shown in FIG. 4.

Figure 5:
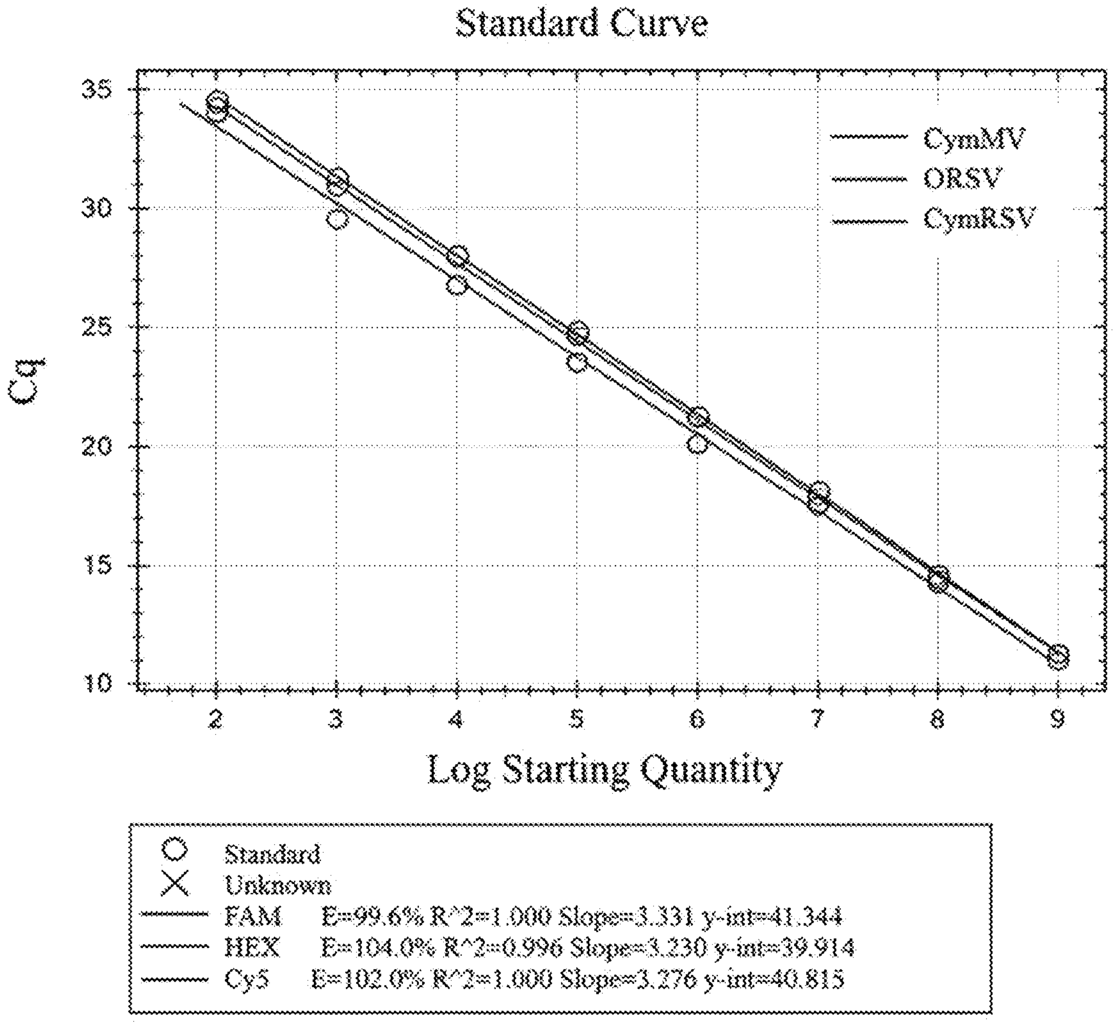
FIG. 5 represents the optimized amplification curves of the real-time fluorescence quantitative PCR system for CymMV, ORSV, and CymRSV provided by a fifth parameter optimization method in Embodiment 3.
Figure 6:
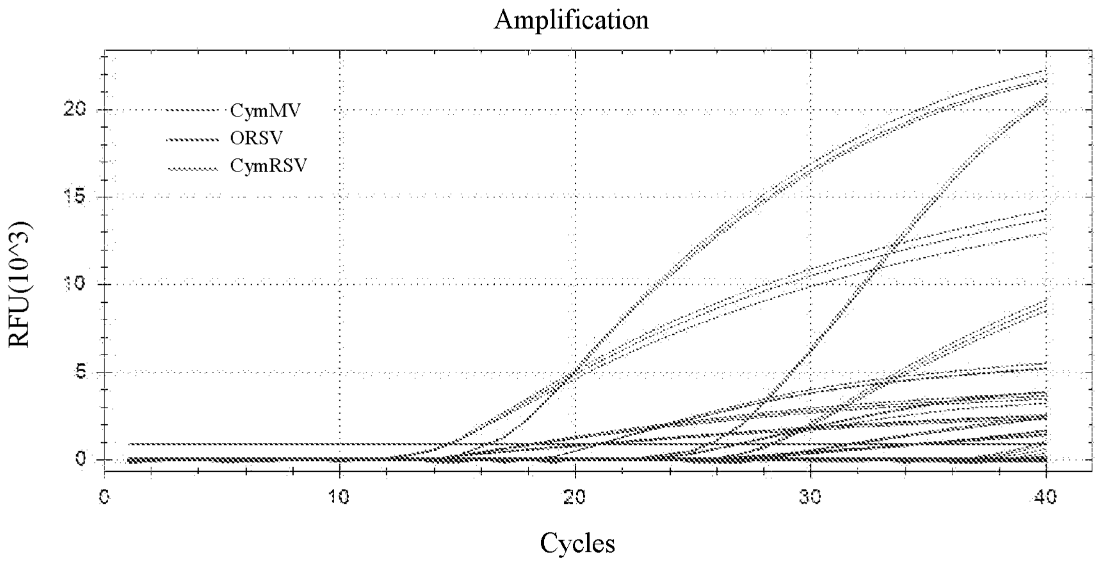
FIG. 6 is an overall figure presenting specific amplification curves (FIG. 7-FIG. 9) of real-time fluorescence quantitative PCR for samples carrying different viruses provided in Embodiment 4 of this specification.
Figure 7:
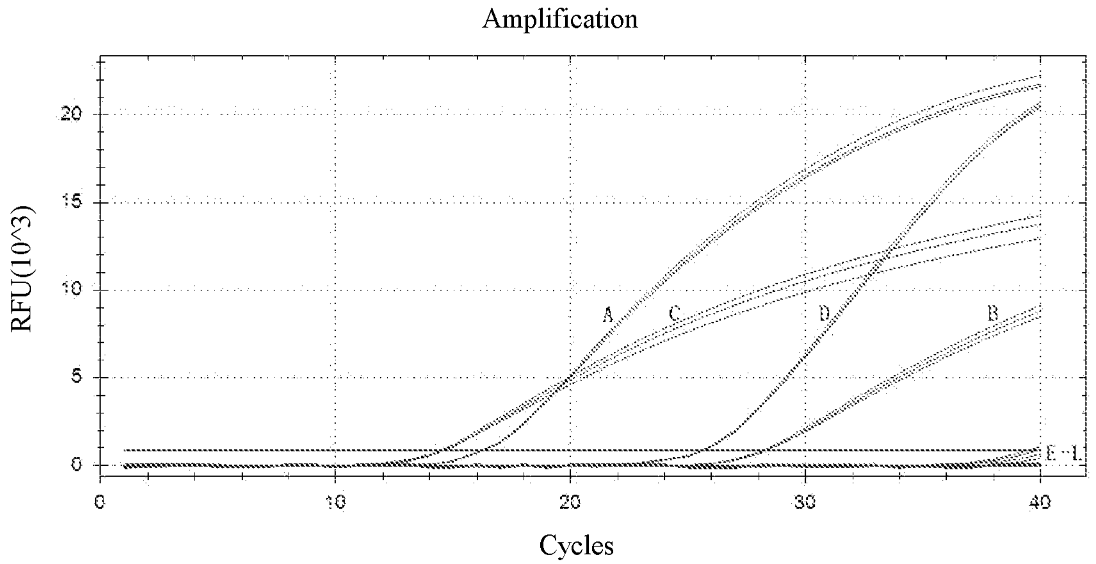
FIG. 7 represents specific amplification curves for CymMV (FAM channel) of real-time fluorescence quantitative PCR for samples carrying different viruses provided in Embodiment 4 of this specification.
Figure 8:
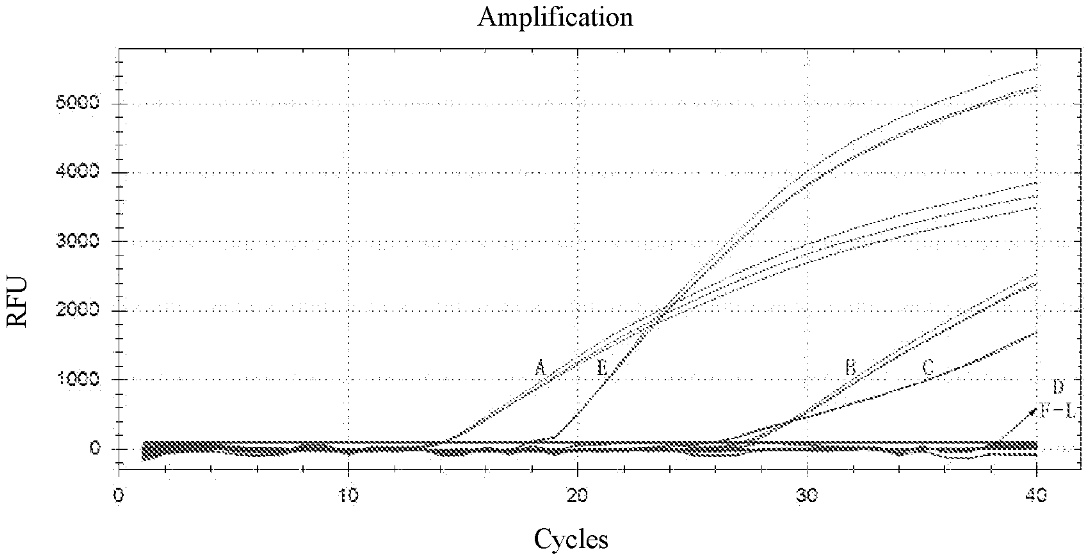
FIG. 8 represents specific amplification curves for ORSV (HEX channel) of real-time fluorescence quantitative PCR for samples carrying different viruses provided in Embodiment 4 of this specification.
Figure 9:
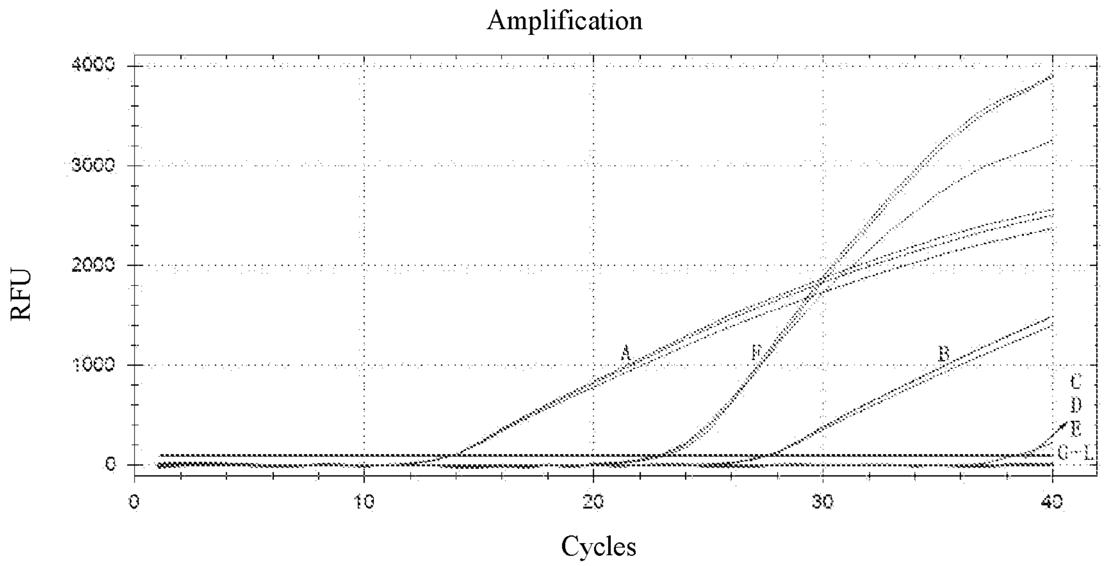
FIG. 9 represents specific amplification curves for CymRSV (Cy5 channel) of real-time fluorescence quantitative PCR for samples carrying different viruses provided in Embodiment 4 of this specification.

The fifth parameter optimization method: the amount of primer for CymMV in the amplification reaction system is 0.5 μL, the amount of probe for CymMV is 1.0 μL, the amount of primer for ORSV is 0.7 μL, the amount of probe for ORSV is 1.4 μL, the amount of primer for CymRSV is 0.6 μL, the amount of probe for CymRSV is 1.2 μL, and the Tm is 60° C. The obtained optimized amplification standard curves of real-time fluorescence quantitative PCR systems for CymMV, ORSV, and CymRSV with different plasmid concentrations are shown in FIG. 5.

(3) Optimal Results:

The optimal annealing temperature is 59° C. The optimal concentrations of primers and probes are as follows: for CymMV: 20 μM of CymMV-F 0.5 μL, 20 μM of CymMV-R 0.5 μL, and 10 μM of CymMV-P 1.0 μL; for ORSV: 10 μM of ORSV-F 0.6 μL, 10 μM of ORSV-R 0.6 μL, and 10 μM of ORSV-P 1.2 μL; for CymRSV: 20 μM of CymRSV-F 0.6 μL, 20 μM of CymRSV-R 0.6 μL, and 10 μM of CymRSV-P 1.2 μL.

The final established real-time fluorescence quantitative PCR optimal amplification reaction system (25 μL): Premix Ex Taq (2×) mixture 12.5 μL, RNase-free $ddH_2O$ 3.7 μL, 20 M CymMV-F 0.5 μL, 20 μM CymMV-R 0.5 μL, 10 μM CymMV-P 1.0 μL, 10 μM ORSV-F 0.6 μL, 10 μM ORSV-R 0.6 μL, 10 μM ORSV-P 1.2 μL, 20 μM CymRSV-F 0.6 μL, 20 μM CymRSV-R 0.6 μL, 10 μM CymRSV-P 1.2 μL, and 2 μL of template cDNA. The amplification program (i.e., the amplification cycle reaction) includes pre-denaturation at 95° C. for 30 seconds; denaturation at 95° C. for 5 seconds, annealing at 59° C. for 30 seconds, and the number of amplification cycles is 40. Collect fluorescence signals of FAM, HEX, and Cy5 at the end of each cycle.

Embodiment 4

Specific Detection

Samples containing a single virus of CymMV, ORSV, or CymRSV, sample containing two viruses of CymMV and ORSV, sample containing three viruses of CymMV, ORSV, and CymRSV, and cDNA samples containing a single virus of Cucumber Mosaic Virus (CMV), Tobacco Mosaic Virus (TMV), Carnation Mottle Virus (CarMV), or Lily Mottle Virus (LMoV) are subjected to specificity tests of triplex simultaneous real-time fluorescence quantitative PCR. Three parallel experiments are performed for each sample.

The results show that, as shown in FIGS. 6 to 9, the cDNA samples containing any one or more viruses from CymMV, ORSV, and CymRSV exhibit specific amplification curves, with a Cq value less than 35, and the test results of other virus are negative. In these figures, the amplification curves for positive sample carrying all three viruses are labeled as A, the amplification curves for sample known to carry all three viruses are labeled as B, the amplification curves for sample known to carry CymMV and ORSV are labeled as C, the amplification curves for sample known to carry CymMV are labeled as D, the amplification curves for sample known to carry ORSV are labeled as E, the amplification curves for sample known to carry CymRSV are labeled as F, and the amplification curves for samples known to carry CMV, TMV, CarMV, or LMoV are labeled as G-J, respectively. The amplification curves for the negative sample are labeled as K, and the amplification curves for $H_2O$ are labeled as L.

Embodiment 5

Establishment of Standard Curves for Real-Time Fluorescence Quantitative PCR

Figure 10:
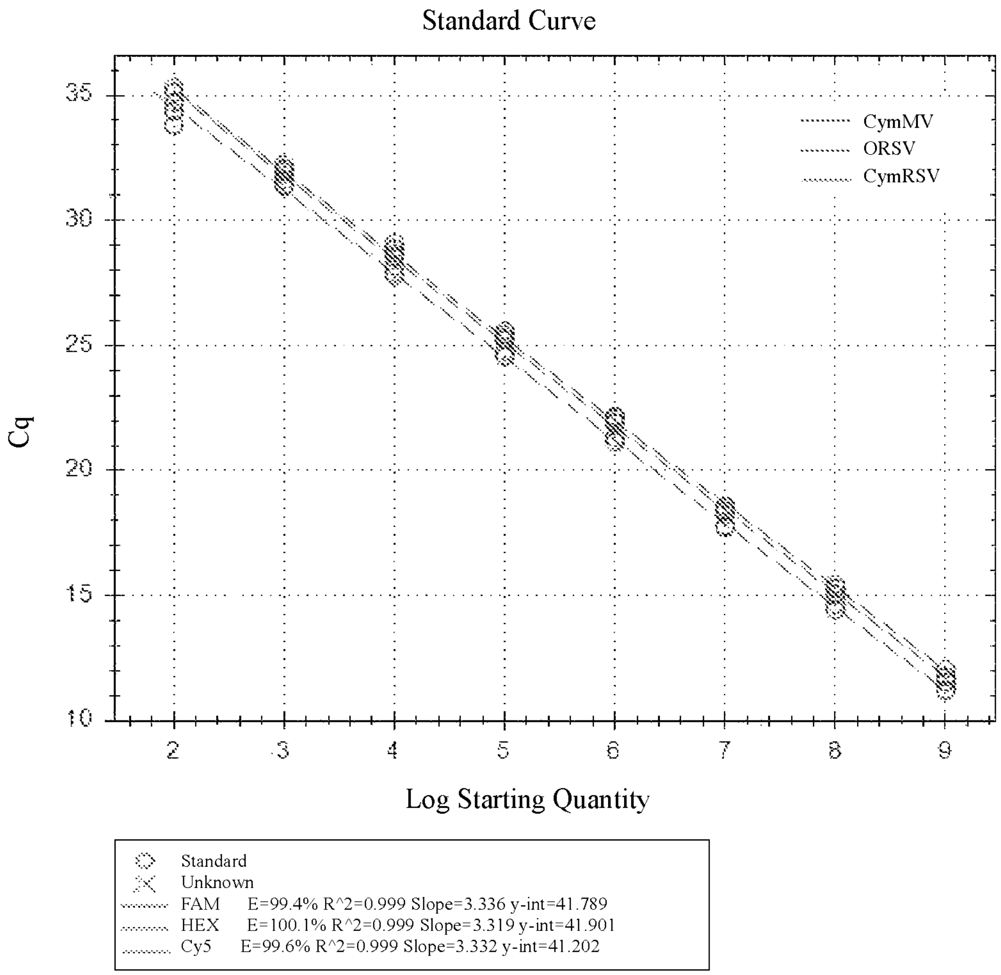
FIG. 10 represents the standard curves and linear equations of the multiplex real-time fluorescence quantitative PCR for CymMV, ORSV, and CymRSV established in Embodiment of this specification.
Figure 11:
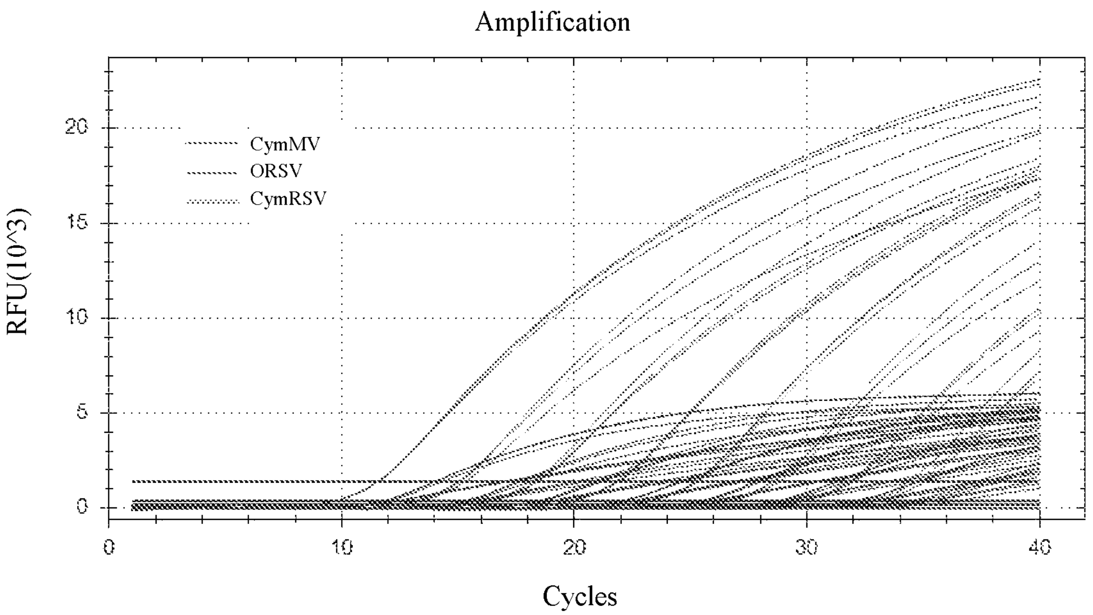
FIG. 11 represents an overall figure presenting the standard amplification curves (FIG. 12-FIG. 14) of the multiplex real-time fluorescence quantitative PCR for CymMV, ORSV, and CymRSV established in Embodiment 5 of this specification.
Figure 12:
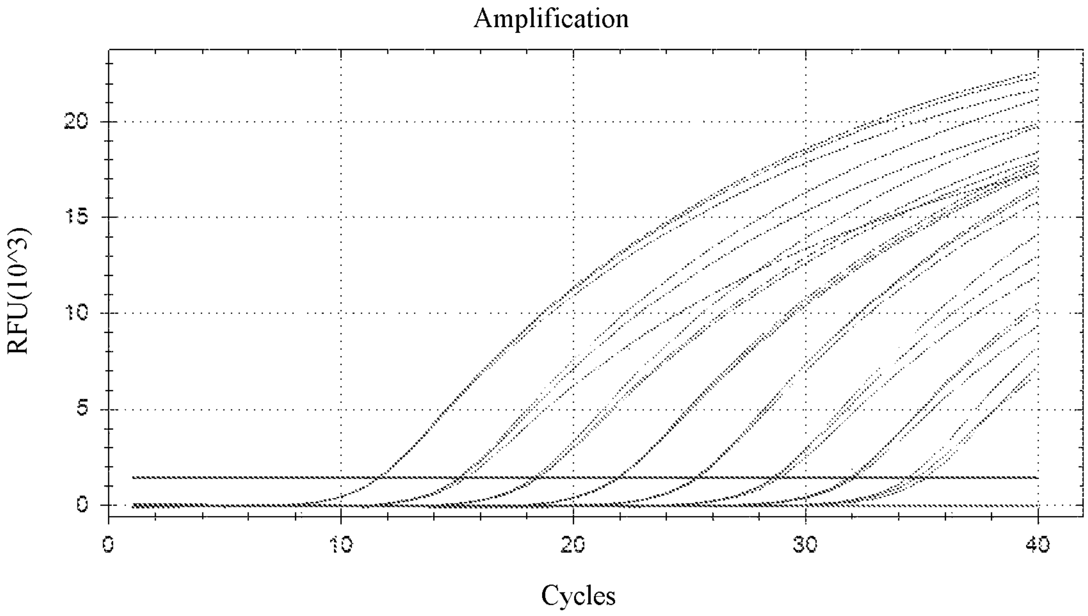
FIG. 12 represents the standard amplification curve for CymMV (FAM channel) of the multiplex real-time fluorescence quantitative PCR established in Embodiment 5 of this specification.
Figure 13:
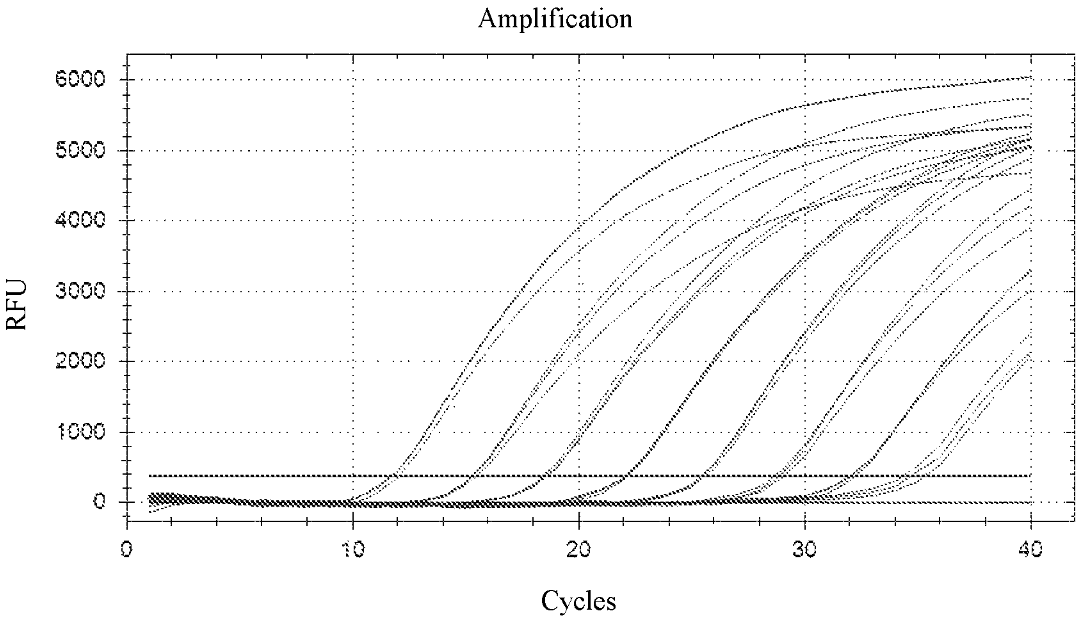
FIG. 13 represents the standard amplification curve for ORSV (HEX channel) of the multiplex real-time fluorescence quantitative PCR established in Embodiment 5 of this specification.
Figure 14:
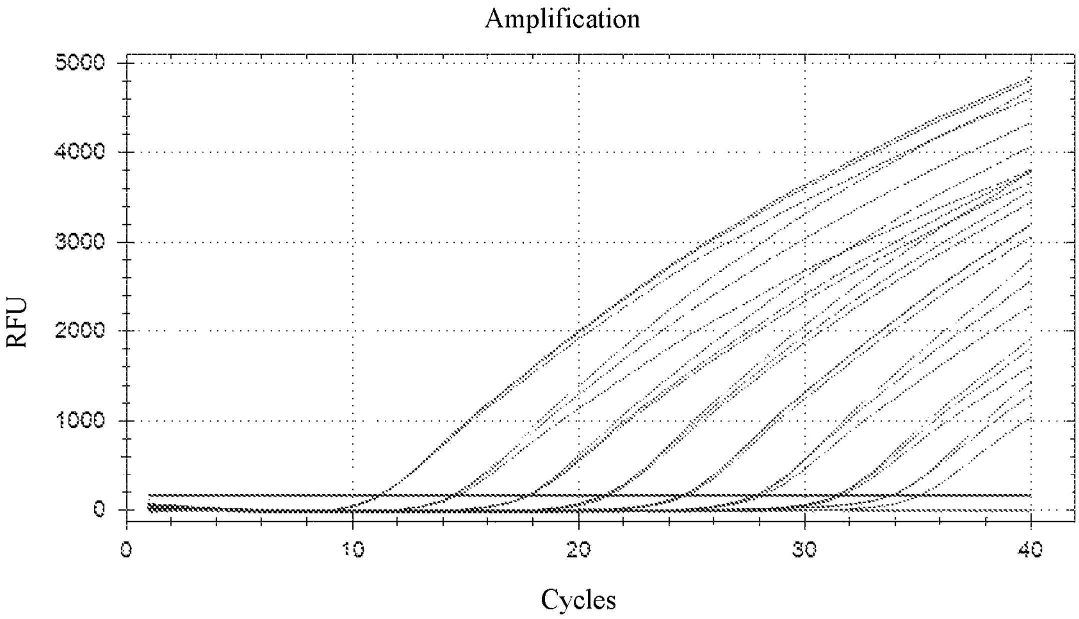
FIG. 14 represents the standard amplification curve for CymRSV (Cy5 channel) of the multiplex real-time fluorescence quantitative PCR established in Embodiment 5 of this specification.
Figure 15:
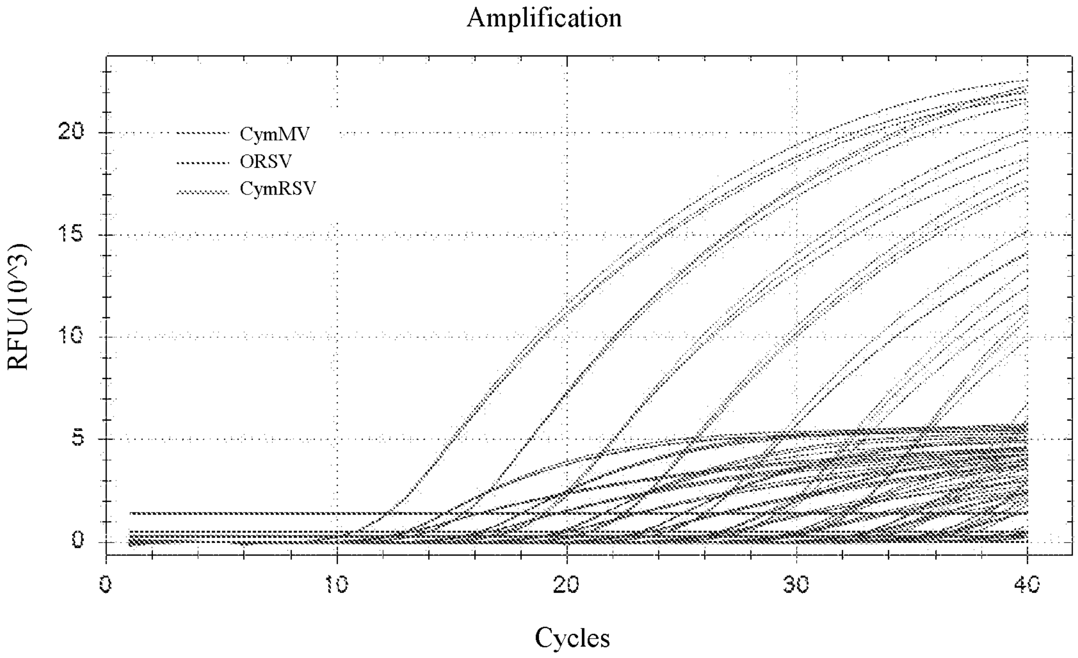
FIG. 15 represents an overall figure presenting the sensitivity amplification curves of the multiplex simultaneous real-time fluorescence quantitative PCR for CymMV, ORSV, and CymRSV in Embodiment 6 of this specification.

EASY Dilution is used to dilute the mixed plasmid standards into 8 gradients from $1\times10^9$ copies to $1\times10^2$ copies according to a 10-fold gradient. qRT-PCR detection is performed under the optimized reaction conditions mentioned above, and three parallel experiments are set for each concentration, to obtain the standard curve amplification charts (as shown in FIGS. 11 to 14) and the standard curve linear equations (as shown in FIG. 10) of the real-time fluorescence quantitative PCR detection for CymMV, ORSV, and CymRSV. The amplification standard curve equations are as follows:

$$\text{CymMV: } y=-3.336x+41.789 (E=99.4\%, R^2=0.999);$$

$$\text{ORSV: } y=-3.319x+41.901 (E=100.1\%, R^2=0.999);$$

$$\text{CymRSV: } y=-3.332x+41.202 (E=99.6\%, R^2=0.999).$$

Here, E represents the amplification efficiency, and $R^2$ represents the coefficient of determination. The results show that the fluorescence curves of the established amplification reaction system have a strong correlation with the concentration of the target gene, and have high accuracy.

Embodiment 6

Application Reliability Test (1) Sensitivity Test

The mixed plasmid standards with concentrations ranging from $10^9$ to $10^2$ copies, are used as templates to perform qRT-PCR amplification (as shown in FIGS. 15 to 18). Conduct three parallel experiments for each concentration. The sensitivity of the triple fluorescence quantitative system is calculated. Here, A: $1\times10^9$ copies; B: $1\times10^8$ copies; C: $1\times10^7$ copies; D: $1\times10^6$ copies; E: $1\times10^5$ copies; F: $1\times10^4$ copies; G: $1\times10^3$ copies; H: $1\times10^2$ copies; f 1×10 copies; J: 1 copy; K: $H_2O$. In this real-time fluorescence quantitative PCR detection method, the stable detection rates of the lower detection limits for CymMV, ORSV, and CymRSV are 10 copies, $10^2$ copies, and $10^2$ copies, respectively, with the highest detection rate for CymMV, ORSV, and CymRSV are all 1 copy, indicating that this method has high sensitivity.

(2) Reproducibility Test for Detecting Three Viruses

Standard plasmid samples with concentrations of $1\times10^4$ copies, $1\times10^5$ copies, $1\times10^6$ copies, $1\times10^7$ copies, and $1\times10^8$ copies are used as templates, and the established real-time fluorescence quantitative PCR is applied for amplification to verify the reproducibility of this method. Intra-group reproducibility tests are conducted with three parallel experiments.

The results (as shown in Table 2) indicate that the coefficient of variation for Cq values in intra-group reproducibility tests is less than 0.95%, and in inter-group reproducibility tests is less than 0.5500, demonstrating that this system has good reproducibility.

TABLE 2

Reproducibility Test of Real-Time Fluorescence Quantitative PCR Detection System

| | Positive plasmid copy number(copies · $\mu L^{-1)}$ | Cq value within group | | | Cq value between groups | | |
|---|---|---|---|---|---|---|---|
| | | Mean | standard deviation | coefficient of variation(%) | Mean | standard deviation | coefficient of variation (%) |
| CymMV | $5\times10^3$ | 28.65 | 0.176 | 0.61 | 28.76 | 0.09 | 0.31 |
| | $5\times10^4$ | 25.25 | 0.054 | 0.21 | 25.32 | 0.05 | 0.19 |
| | $5\times10^5$ | 21.90 | 0.031 | 0.14 | 21.92 | 0.05 | 0.23 |
| | $5\times10^6$ | 18.35 | 0.103 | 0.56 | 18.49 | 0.06 | 0.33 |
| | $5\times10^7$ | 15.15 | 0.140 | 0.92 | 15.19 | 0.08 | 0.51 |
| ORSV | $5\times10^3$ | 28.89 | 0.204 | 0.71 | 28.95 | 0.09 | 0.31 |
| | $5\times10^4$ | 25.49 | 0.090 | 0.35 | 25.45 | 0.07 | 0.29 |
| | $5\times10^5$ | 22.13 | 0.051 | 0.23 | 22.09 | 0.06 | 0.28 |
| | $5\times10^6$ | 18.53 | 0.096 | 0.52 | 18.66 | 0.09 | 0.46 |
| | $5\times10^7$ | 15.36 | 0.100 | 0.65 | 15.35 | 0.05 | 0.32 |
| CymRSV | $5\times10^3$ | 27.95 | 0.193 | 0.69 | 28.22 | 0.09 | 0.31 |
| | $5\times10^4$ | 24.64 | 0.119 | 0.48 | 24.86 | 0.07 | 0.30 |
| | $5\times10^5$ | 21.21 | 0.102 | 0.48 | 21.37 | 0.07 | 0.33 |
| | $5\times10^6$ | 17.76 | 0.035 | 0.20 | 18.04 | 0.03 | 0.15 |
| | $5\times10^7$ | 14.51 | 0.124 | 0.86 | 14.69 | 0.06 | 0.43 |

Embodiment 7

Detection of Phalaenopsis Orchid Samples

The above method is used to simultaneously detect confirmed positive samples of phalaenopsis orchid, negative sample, and eight mixed plasmid standards. The real-time fluorescence quantitative PCR amplification curves are shown in FIGS. 19 to 22, wherein A: $1\times10^9$ copies; B: $1\times10^8$ copies; C: $1\times10^7$ copies; D: $1\times10^6$ copies; E: $1\times10^5$ copies; F: $1\times10^4$ copies; G: $1\times10^3$ copies; H: $1\times10^2$ copies; L: positive sample carrying all three viruses; J: sample known to carry all three viruses; K: sample known to carry CymMV and ORSV, L: sample known to carry CymMV; M: sample known to carry CymRSV, N: negative sample, O: $H_2O$. The test results of positive samples show that the Cq values are all less than 35, while the test results of negative samples show no amplification curves.

In summary:

1. The present invention provides a primer-probe combination and a method for rapid identification of orchid infection with CymMV, ORSV, and CymRSV Design specific detection primers and probes based on the conserved sequences of the coat protein genes of CymMV, ORSV, and CymRSV. By optimizing the amount of primers and probes added and the reaction annealing temperature, the optimal reaction system and procedure were established. The qRT-PCR detection method for CymMV, ORSV, and CymRSV established by the present invention has the advantages of high efficiency, rapidness, and high sensitivity. It can accurately and efficiently detect CymMV, ORSV, and CymRSV in orchid samples for long-term monitoring and early warning and fashion trend research of CymMV, ORSV, and CymRSV.
2. This method is quick and efficient, while ensuring high sensitivity, it only takes one-third of the time of single-gene qRT-PCR technology, and the detection cost is significantly reduced, with each sample detection cost reduced by about ⅓ to ½. Furthermore, this detection method eliminates the need for traditional agarose gel electrophoresis and allows for result determination using the program provided by real-time fluorescence quantitative PCR machines immediately after the reaction.
3. With this invention, all three viruses can be accurately qualitatively or quantitatively determined in a single test. After extracting and reverse-transcribing the total RNA from the sample to cDNA, real-time fluorescence quantitative PCR is performed using cDNA as a template to obtain the Cq values of CymMV, ORSV, and CymRSV. Based on these Cq values, the degree of CymMV, ORSV, and CymRSV infection can be directly determined. Alternatively, the Cq values can be applied to the respective standard curve linear equations to calculate the copy number of the carried viruses, achieving accurate quantification.
4. The present invention exhibits strong specificity as it does not react with Cucumber Mosaic Virus (CMV), Tobacco Mosaic Virus (TMV), Carnation Mottle Virus (CarMV), or Lily Mottle Virus (LMoV). It only produces specific fluorescence signals for samples infected with a single virus or multiple viruses of CymMV, ORSV, and CymRSV.
5. The method has excellent repeatability, with intra-group coefficients of variation all less than 0.95% and inter-group coefficients of variation all less than 0.55%.
6. The method demonstrates high sensitivity, capable of detecting 1 to 10 copies.

It needs to be noted that the embodiments as disclosed are intended to facilitate further understanding of the present disclosure; however, those skilled in the art may understand that various substitutions and modifications are possible without departing from the spirit and scope of the present disclosure. Therefore, the present disclosure should not be limited to the contents disclosed in the embodiments, but should be governed by the appended claims.

This application contains a Sequence Listing XML as a separate part of the disclosure, set forth in accordance with the requirements of 37 CFR-1.831-1.835. The XML file named "P2310110001US.xml", created Dec. 26, 2023, 12,634 bytes in size, is submitted herewith and is incorporated by reference in its entirety.

What is claimed is:

1. A set of primers and probes for simultaneous detection of Cymbidium mosaic virus (CymMV), Odontoglossum ringspot virus (ORSV), and Cymbidium ringspot virus (CymRSV) wherein the set comprises:

```
a forward primer CymMV-F:
                                   (SEQ ID NO: 1)
5'-CTGATGCTGGCCACTAACGA-3';

a reverse primer CymMV-R:
                                   (SEQ ID NO: 2)
5'-CACGTTCACGGTCAGTAGGG-3';

a probe CymMV-P:
                                   (SEQ ID NO: 3)
FAM-CCGCCAACTGGGCCAAGGCT-BHQ1;

a forward primer, ORSV-F:
                                   (SEQ ID NO: 4)
5'-TTGACCAGTAGGTTCCCTGC-3';

a reverse primer ORSV-R:
                                   (SEQ ID NO: 5)
5'-TAGTTGTCGGATTCTGCGGAT-3';

a probe ORSV-P:
                                   (SEQ ID NO: 6)
HEX-TGGTTACTTCAGAGTTTATCGCTATG-BHQ1;

a forward primer CymRSV-F:
                                   (SEQ ID NO: 7)
5'-CGCAGTGGGTGACTTATT-3';

a reverse primer CymRSV-R:
                                   (SEQ ID NO: 8)
5'-CGTCGTGGCTGTGGTAG-3';
and

a probe CymRSV-P:
                                   (SEQ ID NO: 9)
Cy5-CACAGTAACCTTCTACGAACCGCAACCG-BHQ3.
```

2. A method for simultaneous detection of CymMV, ORSV, and CymRSV, comprising:

extracting total RNA from a test sample, synthesizing cDNA, and using cDNA as a template;

conducting real-time fluorescence quantitative PCR amplification cycle reactions using the primers and probes as described in claim 1 in a real-time fluorescence quantitative PCR amplification system to obtain amplification curves and Cq values of CymMV, ORSV, and CymRSV respectively;

constructing plasmid standards of CymMV, ORSV, and CymRSV as templates, and obtaining simultaneous multi-detection standard curves of CymMV, ORSV, and CymRSV, and building standard curve equations for CymMV, ORSV, and CymRSV respectively through fitting; and calculating copy numbers of CymMV, ORSV, and CymRSV in the test sample by substituting the Cq values of CymMV, ORSV, and CymRSV into the standard curve equations of CymMV, ORSV, and CymRSV respectively.

3. The method of claim 2, wherein, the real-time fluorescence quantitative PCR amplification system comprises 12.5 μL of a 2× real-time PCR master mix comprising Taq DNA polymerase, buffer, dNTPs, and $Mg^{2+}$ and 3.7 μL of RNase-free $ddH_2O$.

4. The method of claim 2, wherein, the conducting real-time fluorescence quantitative PCR amplification cycle comprises:

constructing an amplification reaction system, wherein the amplification reaction system comprising:

12.5 μL of a 2× real-time PCR master mix comprising Taq DNA polymerase, buffer, dNTPs, and $Mg^{2+}$,
3.7 μL of RNase-free $ddH_2O$,
0.5 μL of 20 μM of CymMV-F
0.5 μL of 20 μM of CymMV-R,
1.0 μL of 10 μM of CymMV-P,
0.6 μL of 10 μM of ORSV-F,
0.6 μL of 10 μM of ORSV-R,
1.2 μL of 10 μM of ORSV-P,
0.6 μL of 20 μM of CymRSV-F,
0.6 μL of 20 μM of CymRSV-R,
1.2 μL of 10 μM of CymRSV-P, and
2 μL of the cDNA of the test sample;

performing the amplification cycle reactions utilizing the amplification reaction system.

5. The method of claim 2, wherein, the standard curve equations for CymMV, ORSV, and CymRSV are respectively as follows:

CymMV: $y=-3.336x+41.789$ ($E=99.4\%$, $R^2=0.999$);
ORSV: $y=-3.319x+41.901$ ($E=100.1\%$, $R^2=0.999$);
CymRSV: $y=-3.332x+41.202$ ($E=99.6\%$, $R^2=0.999$);
wherein E is amplification efficiency, and $R^2$ is a correlation coefficient.

6. The method of claim 2, further comprising: determining whether CymMV, ORSV, or CymRSV exists in the test sample based on the amplification curves and the Cq values of CymMV, ORSV, and CymRSV, a determination method comprising:

if there are no amplification curves for CymMV, ORSV, and CymRSV in the test sample after the real-time fluorescence quantitative PCR amplification cycle reactions, then CymMV, ORSV, and CymRSV are determined to be negative;

if there are amplification curves present, then analyzing the Cq values to determine whether the sample is positive or negative, wherein:

if any of the Cq values of CymMV, ORSV, or CymRSV is less than or equal to 35, then a virus corresponding to the Cq value less than or equal to 35 is determined to be positive;

if any of the Cq values of CymMV, ORSV, or CymRSV is within a range of 35-40, a retest is performed to obtain a first test result, if the first test result indicates that the Cq value previously within the range of 35-40 is still within the range of 35-40 or less than 35, then a virus corresponding to the Cq value within the range of 35-40 or less than 35 is determined to be positive.

7. The method of claim 2, the conducting real-time fluorescence quantitative PCR amplification cycle reactions comprises:

a) an initial denaturation step within a temperature range of 94° C. to 95° C. for 30 seconds; and b) performing 40 amplification cycles of the following amplification cycle: denaturation within a temperature range of 94° C. to 95° C. for 5 seconds and annealing within a temperature range of 58° C. to 60° C. for 30 seconds.

8. The method of claim 2, the conducting real-time fluorescence quantitative PCR amplification cycle reactions comprises:

a) an initial denaturation step pre-denaturation at 95° C. for 30 seconds; and b) performing 40 amplification cycles of the following amplification cycle: denaturation at 95° C. for 5 seconds and annealing at 59° C. for 30 seconds.

* * * * *

SEQUENCE LISTING

```
Sequence total quantity: 9
SEQ ID NO: 1            moltype = AA  length = 20
FEATURE                 Location/Qualifiers
REGION                  1..20
                        note = sequence of forward primer for detection of CymMV
source                  1..20
                        mol_type = protein
                        organism = synthetic construct
SEQUENCE: 1
CTGATGCTGG CCACTAACGA                                              20

SEQ ID NO: 2            moltype = DNA  length = 20
FEATURE                 Location/Qualifiers
misc_feature            1..20
                        note = sequence of reverse primer for detection of CymMV
source                  1..20
                        mol_type = other DNA
                        organism = synthetic construct
SEQUENCE: 2
cacgttcacg gtcagtaggg                                              20

SEQ ID NO: 3            moltype = DNA  length = 20
FEATURE                 Location/Qualifiers
misc_feature            1..20
                        note = sequence of probe for detection of CymMV
source                  1..20
                        mol_type = other DNA
                        organism = synthetic construct
SEQUENCE: 3
ccgccaactg ggccaaggct                                              20

SEQ ID NO: 4            moltype = DNA  length = 20
FEATURE                 Location/Qualifiers
misc_feature            1..20
                        note = sequence of forward primer for detection of ORSV
source                  1..20
                        mol_type = other DNA
                        organism = synthetic construct
SEQUENCE: 4
ttgaccagta ggttccctgc                                              20

SEQ ID NO: 5            moltype = DNA  length = 21
FEATURE                 Location/Qualifiers
misc_feature            1..21
                        note = sequence of reverse primer for detection of ORSV
source                  1..21
                        mol_type = other DNA
                        organism = synthetic construct
SEQUENCE: 5
tagttgtcgg attctgcgga t                                            21

SEQ ID NO: 6            moltype = DNA  length = 26
FEATURE                 Location/Qualifiers
misc_feature            1..26
                        note = sequence of probe for detection of ORSV
source                  1..26
                        mol_type = other DNA
                        organism = synthetic construct
SEQUENCE: 6
tggttacttc agagtttatc gctatg                                       26

SEQ ID NO: 7            moltype = DNA  length = 18
FEATURE                 Location/Qualifiers
misc_feature            1..18
                        note = sequence of forward primer for detection of CymRSV
source                  1..18
                        mol_type = other DNA
                        organism = synthetic construct
SEQUENCE: 7
cgcagtgggt gacttatt                                                18
```

-continued

```
SEQ ID NO: 8           moltype = DNA  length = 17
FEATURE                Location/Qualifiers
misc_feature           1..17
                       note = sequence of reverse primer for detection of CymRSV
source                 1..17
                       mol_type = other DNA
                       organism = synthetic construct
SEQUENCE: 8
cgtcgtggct gtggtag                                                 17

SEQ ID NO: 9           moltype = DNA  length = 28
FEATURE                Location/Qualifiers
misc_feature           1..28
                       note = sequence of probe for detection of CymRSV
source                 1..28
                       mol_type = other DNA
                       organism = synthetic construct
SEQUENCE: 9
cacagtaacc ttctacgaac cgcaaccg                                     28
```